(12) United States Patent
Yuan et al.

(10) Patent No.: US 11,661,531 B2
(45) Date of Patent: May 30, 2023

(54) HYGIENE ADHESIVES COMPRISING LOW VOLATILE TACKIFIER COMPOSITIONS

(71) Applicant: Synthomer Adhesive Technologies LLC, Beachwood, OH (US)

(72) Inventors: Bing Yuan, Methuen, MA (US); James Palmer Dickerson, Kingsport, TN (US); Bee Kim Liew, Kingsport, TN (US); Christopher Wayne Osborne, Johnson City, TN (US); Jacobus Siera, Hoogerheide (NL)

(73) Assignee: Synthomer Adhesives Technology LLC, Beachwood, OH (US)

(*) Notice: Subject to any disclaimer, the term of this patent is extended or adjusted under 35 U.S.C. 154(b) by 291 days.

(21) Appl. No.: 16/775,980

(22) Filed: Jan. 29, 2020

(65) Prior Publication Data
US 2020/0248044 A1   Aug. 6, 2020

Related U.S. Application Data

(60) Provisional application No. 62/841,498, filed on May 1, 2019, provisional application No. 62/841,511, filed on May 1, 2019, provisional application No. 62/841,515, filed on May 1, 2019, provisional application No. 62/841,507, filed on May 1, 2019, provisional application No. 62/799,383, filed on Jan. 31, 2019.

(51) Int. Cl.
| | | |
|---|---|---|
| *C08L 53/02* | (2006.01) | |
| *C09J 11/08* | (2006.01) | |
| *C09J 11/06* | (2006.01) | |
| *C09J 123/26* | (2006.01) | |
| *A61L 15/20* | (2006.01) | |
| *A61L 15/58* | (2006.01) | |
| *A61L 15/22* | (2006.01) | |
| *C09J 153/02* | (2006.01) | |
| *C08K 5/3435* | (2006.01) | |
| *C08K 5/13* | (2006.01) | |
| *C08K 5/375* | (2006.01) | |
| *C08K 5/372* | (2006.01) | |
| *C08K 5/3492* | (2006.01) | |
| *C08K 5/134* | (2006.01) | |
| *C08K 5/52* | (2006.01) | |
| *C08K 5/5393* | (2006.01) | |
| *C09J 7/38* | (2018.01) | |
| *C08L 23/08* | (2006.01) | |
| *C08L 23/26* | (2006.01) | |
| *C09J 123/08* | (2006.01) | |
| *C08K 5/00* | (2006.01) | |
| *C08K 5/105* | (2006.01) | |
| *C08K 5/12* | (2006.01) | |

(52) U.S. Cl.
CPC .......... *C08L 53/02* (2013.01); *A61L 15/20* (2013.01); *A61L 15/225* (2013.01); *A61L 15/585* (2013.01); *C08K 5/13* (2013.01); *C08K 5/1345* (2013.01); *C08K 5/3435* (2013.01); *C08K 5/3492* (2013.01); *C08K 5/372* (2013.01); *C08K 5/375* (2013.01); *C08K 5/52* (2013.01); *C08K 5/5393* (2013.01); *C08L 23/0853* (2013.01); *C08L 23/26* (2013.01); *C09J 7/381* (2018.01); *C09J 11/06* (2013.01); *C09J 11/08* (2013.01); *C09J 123/0853* (2013.01); *C09J 123/26* (2013.01); *C09J 153/02* (2013.01); *C08K 5/005* (2013.01); *C08K 5/105* (2013.01); *C08K 5/12* (2013.01); *C08K 5/34926* (2013.01); *C09J 2301/408* (2020.08); *C09J 2301/414* (2020.08); *C09J 2453/00* (2013.01)

(58) Field of Classification Search
CPC ...... C09J 153/02; C08K 5/005; C08K 5/3435; C08K 5/13; C08F 8/04
See application file for complete search history.

(56) References Cited

U.S. PATENT DOCUMENTS

| | | | |
|---|---|---|---|
| 3,032,533 A | 5/1962 | Patterson et al. | |
| 3,468,837 A | 9/1969 | Wheeler et al. | |
| 3,577,398 A | 5/1971 | Pace et al. | |
| 3,622,551 A * | 11/1971 | Davis | C09J 109/06 526/221 |

(Continued)

FOREIGN PATENT DOCUMENTS

| | | |
|---|---|---|
| CN | 1027541 C | 2/1995 |
| CN | 1137164 C | 2/2004 |

(Continued)

OTHER PUBLICATIONS

Machine translation of JP-2003213073-A (2003, pages).*

(Continued)

*Primary Examiner* — Brieann R Johnston
(74) *Attorney, Agent, or Firm* — Walter Ottesen, P.A.

(57) ABSTRACT

A tackifier composition comprising at least one thermoplastic hydrocarbon resin and an antioxidant composition is provided; wherein a portion of the volatile organic compounds in the thermoplastic hydrocarbon resin has been removed; wherein the antioxidant composition comprises at least one primary antioxidant and at least one secondary antioxidant; and wherein the levels of individual volatile organic compound monitored in the tackifier composition are less than about 0.5 ppm as measured by GC/MS headspace analysis. Processes for producing the tackifier composition are also provided as well as adhesives comprising the tackifier compositions.

19 Claims, No Drawings

(56) References Cited

U.S. PATENT DOCUMENTS

| | | | |
|---|---|---|---|
| 3,701,760 | A | 10/1972 | Hagemeyer, Jr. et al. |
| 4,068,062 | A | 1/1978 | Lepert |
| 4,160,692 | A | 7/1979 | Mitchell et al. |
| 4,164,427 | A * | 8/1979 | Godfrey ................ C08K 5/372 524/307 |
| 4,330,655 | A | 5/1982 | Bullard |
| 4,514,554 | A | 4/1985 | Hughes et al. |
| 4,683,268 | A * | 7/1987 | Ahner .................... C09J 109/06 525/232 |
| 5,128,397 | A * | 7/1992 | Horsey .................. C09J 123/08 524/564 |
| 5,177,133 | A * | 1/1993 | Peck ........................ C09F 1/04 524/270 |
| 5,552,489 | A | 9/1996 | Merrill et al. |
| 5,652,308 | A | 7/1997 | Merrill et al. |
| 5,723,222 | A * | 3/1998 | Sato ........................ C09J 153/02 428/512 |
| 6,143,814 | A | 11/2000 | Schiller et al. |
| 6,232,376 | B1 | 5/2001 | Tsukada et al. |
| 6,329,468 | B1 | 12/2001 | Wang |
| 6,344,515 | B1 | 2/2002 | Parikh et al. |
| 6,451,964 | B1 | 9/2002 | Hakamaya et al. |
| 6,458,902 | B1 * | 10/2002 | Okazaki .................... C08F 8/04 526/346 |
| 6,541,547 | B1 | 4/2003 | Schmutz et al. |
| 6,664,317 | B2 | 12/2003 | King, III |
| 6,756,451 | B2 | 6/2004 | Belt et al. |
| 6,770,693 | B2 | 8/2004 | Stein et al. |
| 6,787,591 | B2 | 9/2004 | Koch et al. |
| 6,825,302 | B1 | 11/2004 | Cottman et al. |
| 6,984,428 | B2 | 1/2006 | Krawinkel et al. |
| 6,989,423 | B2 | 1/2006 | Wagner et al. |
| 7,018,570 | B2 | 3/2006 | Haruna et al. |
| 7,157,511 | B2 | 1/2007 | Bobsein et al. |
| 7,169,835 | B2 | 1/2007 | Gugumus |
| 7,265,171 | B2 | 9/2007 | Leppard et al. |
| 7,312,254 | B2 | 12/2007 | Goodrich et al. |
| 7,468,410 | B2 | 12/2008 | Chafin et al. |
| 7,645,851 | B2 | 1/2010 | Berndsen et al. |
| 7,875,663 | B2 | 1/2011 | Keck-Antoine et al. |
| 7,910,642 | B2 | 3/2011 | Mäder et al. |
| 7,935,780 | B2 | 5/2011 | Hong et al. |
| 7,947,768 | B2 | 5/2011 | Basfar et al. |
| 8,008,383 | B2 | 8/2011 | Gelbin et al. |
| 8,008,384 | B2 | 8/2011 | Gelbin et al. |
| 8,058,356 | B2 | 11/2011 | Kao et al. |
| 8,080,618 | B2 | 12/2011 | Kim et al. |
| 8,501,846 | B2 | 8/2013 | Zenner et al. |
| 8,507,161 | B2 | 8/2013 | Wu et al. |
| 8,628,699 | B2 | 1/2014 | Meyer et al. |
| 8,629,204 | B2 | 1/2014 | Basfar et al. |
| 8,653,154 | B2 | 2/2014 | Morrison et al. |
| 8,921,474 | B2 | 12/2014 | Alper et al. |
| 9,034,976 | B2 | 5/2015 | Kashima |
| 9,156,963 | B2 | 10/2015 | Morrison et al. |
| 9,279,052 | B2 | 3/2016 | Kim et al. |
| 9,428,597 | B2 | 8/2016 | Price et al. |
| 9,469,791 | B2 | 10/2016 | Knutson et al. |
| 9,481,816 | B2 | 11/2016 | Takenaka |
| 9,555,161 | B2 | 1/2017 | Morrison et al. |
| 9,644,043 | B2 | 5/2017 | Miyamoto et al. |
| 9,725,579 | B2 | 8/2017 | Gupta et al. |
| 9,840,571 | B2 | 12/2017 | Dooley |
| 9,868,879 | B2 | 1/2018 | Schneider |
| 9,926,472 | B2 | 3/2018 | Tan et al. |
| 9,963,561 | B2 | 5/2018 | Waldie et al. |
| 9,971,267 | B2 | 5/2018 | Morrison et al. |
| 9,988,518 | B2 | 6/2018 | Lacroix et al. |
| 10,093,788 | B2 | 10/2018 | Cogen et al. |
| 10,100,193 | B2 | 10/2018 | Sohn et al. |
| 10,119,010 | B2 | 11/2018 | Torchia et al. |
| 10,196,514 | B2 | 2/2019 | Ohashi et al. |
| 10,214,627 | B2 | 2/2019 | Van Mierloo et al. |
| 10,457,764 | B2 | 10/2019 | Kameyama et al. |
| 2003/0021917 | A1 | 1/2003 | Hotaka et al. |
| 2005/0182186 | A1 | 8/2005 | Gielens et al. |
| 2008/0286570 | A1 | 11/2008 | Coutey et al. |
| 2012/0123033 | A1 | 5/2012 | Lederer et al. |
| 2016/0319047 | A1 | 11/2016 | Miyamoto et al. |
| 2017/0073556 | A1 | 3/2017 | Tripathy et al. |
| 2019/0194501 | A1 | 6/2019 | Eckhardt et al. |
| 2021/0230464 | A1 | 7/2021 | Turner et al. |

FOREIGN PATENT DOCUMENTS

| | | | | |
|---|---|---|---|---|
| CN | 102140153 | A | 8/2011 | |
| CN | 101967214 | B | 7/2012 | |
| CN | 102002130 | B | 7/2012 | |
| CN | 101700990 | A | 9/2012 | |
| CN | 102924659 | A | 2/2013 | |
| CN | 102002131 | B | 4/2013 | |
| CN | 102382259 | A | 12/2013 | |
| CN | 104448141 | A | 3/2015 | |
| CN | 106221629 | B | 12/2016 | |
| CN | 106753089 | A | 5/2017 | |
| CN | 107325228 | A | 11/2017 | |
| CN | 104788617 | B | 6/2018 | |
| CN | 109207073 | A | 1/2019 | |
| CN | 106633607 | A | 3/2019 | |
| CN | 106893056 | B | 6/2019 | |
| EP | 0 260 001 | B1 | 11/1990 | |
| EP | 0 936 229 | B1 | 4/2004 | |
| EP | 1 035 143 | B1 | 7/2005 | |
| EP | 3 156 466 | A1 | 4/2017 | |
| EP | 3 854 365 | A1 | 7/2021 | |
| GB | 598 354 | A | 2/1948 | |
| GB | 2 169 909 | A | 7/1986 | |
| JP | 2003213073 | A * | 7/2003 | |
| JP | 2005015767 | A * | 1/2005 | .......... C08L 23/0853 |
| JP | 2006274191 | A * | 10/2006 | |
| JP | 2014051631 | A * | 3/2014 | ............. C08L 23/04 |
| WO | WO 1989 03848 | A1 | 5/1989 | |
| WO | WO 98 22214 | A1 | 5/1998 | |
| WO | WO 2002 014392 | A1 | 2/2002 | |
| WO | WO 2008 097681 | A1 | 8/2008 | |
| WO | WO 2014 176119 | A1 | 10/2014 | |
| WO | WO 2017 171025 | A1 | 10/2014 | |
| WO | WO 2016 184932 | A1 | 11/2016 | |
| WO | 2017086096 | A1 | 5/2017 | |
| WO | WO 2017 137454 | A1 | 8/2017 | |

OTHER PUBLICATIONS

Machine translation of JP-2006274191-A (2006, pages).*
Machine translation of JP-2005015767-A (2005, pages).*
Machine translation of JP-2014051631-A (2014, pages).*
Notification of Transmittal of the International Search Report and the Written Opinion of the International Searching Authority, or the Declaration dated Jun. 12, 2020 received in International Application No. PCT/US20/16034.
Notification of Transmittal of the International Search Report and the Written Opinion of the International Searching Authority, or the Declaration dated Jun. 16, 2020 received in International Application No. PCT/US20/16039.
Invitation to Pay Additional Fees and, where Applicable, Protest Fee dated Mar. 19, 2020 received in International Application No. PCT/US20/16034.
Notification of Transmittal of the International Search Report and the Written Opinion of the International Searching Authority, or the Declaration dated Apr. 2, 2020 received in International Application No. PCT/US20/16041.
Notification of Transmittal of the International Search Report and the Written Opinion of the International Searching Authority, or the Declaration dated Apr. 2, 2020 received in International Application No. PCT/US20/16044.
Invitation to Pay Additional Fees and, where Applicable, Protest Fee dated Apr. 14, 2020 received in International Application No. PCT/US20/16039.
Notification of Transmittal of the International Search Report and the Written Opinion of the International Searching Authority, or the

(56) References Cited

OTHER PUBLICATIONS

Declaration dated Apr. 27, 2020 received in International Application No. PCT/US20/16042.
Bowen, W. R. and Mohammad, A. W.; "Characterization and Prediction of Nonfiltration Membrane Performance—A General Assessment"; Institution of Chemical Engineers; vol. 76, Part A; Nov. 1998; pp. 885-893.
Lesec, James; "Preparative Gel Permeation Chromatography"; Journal of Liquid Chromatography; 8(5); 1985; pp. 875-923.
Loadman, M. J. R.; "Chapter 6—Quantitative elemental analysis"; Analysis of Rubber and Rubber-like Polymers; 1998; pp. 95-128.
Striegel, André M. et al.; "Chapter 13 Oligomeric SEC"; Modern Size-Exclusion Liquid Chromatography: Practice of Gel Permeation and Gel Filtration Chromatography, Second Edition; 2009; pp. 339-367.
Tanco, Margot and Tanaka, David A. Pacheco; "Recent Advances on Carbon Molecular Sieve Membranes (CMSMs) and Reactors"; Processes; 4(29); 2016; 21 pages.
Co-pending U.S. Appl. No. 16/775,932, filed Jan. 29, 2020; Yuan et al.
Co-pending U.S. Appl. No. 16/775,948, filed Jan. 29, 2020; Yuan et al.
Co-pending U.S. Appl. No. 16/775,962, filed Jan. 29, 2020; Yuan et al.
Co-pending U.S. Appl. No. 16/775,999, filed Jan. 29, 2020; Yuan et al.
Extended European Search Report of the European Patent Office dated Oct. 19, 2022 in European patent application 20748398.3.
Supplementary Partial European Search Report of the European Patent Office dated Oct. 19, 2022 in European patent application 20747811.
Supplementary Partial European Search Report of the European Patent Office dated Sep. 12, 2022 in European patent application 20748146.
Supplementary European Search Report of the European Patent Office dated Dec. 13, 2022 in European patent application 20748146.
Supplementary European Search Report of the European Patent Office dated Oct. 19, 2022 in European patent application 20747942.
Supplementary Partial European Search Report of the European Patent Office dated Oct. 19, 2022 in European patent application 20749745.
BASF Se et al, "Additives for Adhesives and Sealants Additives for top performance", May 1, 2013, XP055967819, www.basf.com/global/documents/en/products-and-industries/architectural-coatings/20130501_Additives_for_Adhesives_and_Sealants_Catalogue_Europe.pdf, pp. 1 to 24.
De San Luis, Alicia et al, "Removal of Volatile Organic Compounds from Bulk and Emulsion Polymers: A Comprehensive Survey of the Existing Techniques", Industrial & Engineering Chemistry Research, vol. 58, No. 27, May 27, 2019, pp. 11601 to 11623, XP055887789.

* cited by examiner

HYGIENE ADHESIVES COMPRISING LOW VOLATILE TACKIFIER COMPOSITIONS

CROSS-REFERENCE TO RELATED APPLICATIONS

This application claims the benefit of U.S. Provisional Application No. 62/799,383 filed Jan. 31, 2019 and U.S. Provisional Application Nos. 62/841,498, 62/841,507, 62/841,511, and 62/841,515 all filed May 1, 2019; the entire contents of the provisional applications are hereby incorporated by reference.

BACKGROUND OF THE INVENTION

Public concern for the potential adverse health effects of chemicals released from personal hygiene products and other consumer goods is rising worldwide. Concern translates to pressure on marketers, formulators and chemical raw materials suppliers to work together to reduce odor, volatile organic compounds (VOCs) and trace chemicals in these goods. Thermoplastic hydrocarbon resins are utilized in adhesives used in consumer goods as well as personal hygiene products.

To lower the viscosity sufficiently to enable coating onto a consumer goods, adhesives are applied at high temperatures. For example, most personal hygiene manufacturers heat the adhesive to temperatures exceeding 130° C. before application to nonwoven materials. Volatile substances in the raw materials of the adhesive may be released during this coating process, and additional VOCs can be created by chemical reactions that occur in the adhesive composition. For example, VOCs can be generated due to degradation of thermoplastic hydrocarbon resins during down stream blending or/and dispensing processes. These substances may be vented to the environment or absorbed by other personal hygiene article components, such as nonwoven webs. Because hot melt adhesives function by cooling rapidly to form a strong bond between two substrates, they can also 'lock in' VOCs from any source. Often times, personal hygiene goods are sealed into plastic packaging immediately after manufacturing. Personal hygiene article manufacturing is a high-speed process; no opportunity for venting VOCs exists prior to consumer use of the product. When the consumer opens the packaging, they may notice the odor caused by whichever odorous volatile substances are present in concentrations high enough for the consumer to perceive.

Thermoplastic hydrocarbon resins (tackifiers) are one of the critical components of adhesives for hygiene, packaging, automotive, woodworking and other applications. Therefore, there is a need in these industries for thermoplastic hydrocarbon resins having lower odor and volatile organic compound content and when processed into adhesives and consumer goods, less or no odor causing compounds and/or volatile organic compounds are generated.

BRIEF SUMMARY OF THE INVENTION

In one embodiment of the invention, a tackifier composition comprising at least one thermoplastic hydrocarbon resin and an antioxidant composition; wherein a portion of the volatile organic compounds in the thermoplastic hydrocarbon resin has been removed; wherein the antioxidant composition comprises at least one primary antioxidant and at least one secondary antioxidant; and wherein the levels of individual volatile organic compounds monitored of in the tackifier composition are less than about 0.5 ppm as measured by GC/MS headspace analysis as described in this disclosure.

In another embodiment of the invention, a tackifier composition is provided comprising at least one thermoplastic hydrocarbon resin and an antioxidant composition; wherein a portion of the volatile organic compounds in the thermoplastic hydrocarbon resin has been removed; wherein the antioxidant composition comprises at least one primary antioxidant, optionally at least one secondary antioxidant, and at least one hindered amine light stabilizer (HALS); and wherein the levels of individual volatile organic compound monitored in the tackifier composition are less than about 0.5 ppm as measured by GC/MS headspace analysis described in this disclosure.

In another embodiment of the invention, a process for producing a tackifier composition is provided comprising: a) removing a portion of the volatile organic compounds from a thermoplastic hydrocarbon resin; and b) adding an antioxidant composition to the thermoplastic hydrocarbon resin; wherein the adding is completed by at least one of the following methods: i) at least a portion of at least one antioxidant of the antioxidant composition is added to the thermoplastic hydrocarbon resin prior to step (a); ii) at least a portion of at least one antioxidant in the antioxidant composition is added to the thermoplastic hydrocarbon resin after step (a); iii) at least a portion of at least one antioxidant in the antioxidant composition is added to the thermoplastic hydrocarbon resin before and after step (a) to produce the tackifier composition; wherein the antioxidant composition comprises at least one primary antioxidant, optionally one secondary antioxidant, and at least one hindered amine light stabilizer (HALS); and wherein the levels of individual volatile organic compound monitored in the tackifier composition are less than about 0.5 ppm as measured by GC/MS headspace analysis described in this specification.

In another embodiment of this invention, an adhesive is provided comprising the tackifier compositions previously described.

In another embodiment of this invention, an article is provided comprising the adhesive.

This invention focuses on reducing odor and VOCs of any thermoplastic hydrocarbon resins and tackifier compositions. Odor and VOC levels of the hydrocarbon resins are of great importance for several applications, such as, but not limited to, hygiene, packaging, product assembly and building/constructions. Specifically, in hygiene applications, odor can be caused by certain monomers and/or solvents which either exist in the thermoplastic hydrocarbon resin or are generated during downstream customers' blending processes. Therefore, reducing levels of these volatiles and preventing their generation under customers' process conditions are two effective ways to reduce odor of thermoplastic hydrocarbon resins. In relation to odor, the invention is targeted to reduce the level of certain volatile compounds in partially or fully hydrogenated thermoplastic hydrocarbon resins. These VOCs of interest may cause odor and/or possess potential adverse health effect to human bodies. The total volatile levels will also be certainly reduced significantly with the solutions of this invention. The levels of individual volatiles of interest can be measured by Headspace GCMS under different conditions.

The steam stripping proposed in this invention can effectively reduce the volatile organic compound content of thermoplastic hydrocarbon resins.

The solutions in this invention include, but are not limited to:

(1) Steam stripping to remove odor related volatile organic compounds; and
(2) Effective antioxidant packages to stabilize thermoplastic hydrocarbon resins, so they do not generate additional VOCs or oligomers in customers' blending process.

A portion of the volatile organic compounds has been removed from thermoplastic hydrocarbon resins by various methods, and various antioxidants have been used to help prevent degradation and thus the generation of VOCs. However, the combination of this antioxidant composition and removal of oligomers by steam stripping is not known in the art, and provides a tackifier composition with the levels of individual VOCs monitored less than about 0.5 ppm as measured by GC/MS headspace analysis described in this disclosure.

DETAILED DESCRIPTION OF THE INVENTION

In one embodiment of the invention, a tackifier composition is provided comprising at least one thermoplastic hydrocarbon resin and an antioxidant composition; wherein a portion of the volatile organic compounds in the thermoplastic hydrocarbon resin has been removed; wherein the antioxidant composition comprises at least one primary antioxidant, optionally at least one secondary antioxidant, and at least one hindered amine light stabilizer (HALS); and wherein the levels of individual volatile organic compounds of interest in the tackifier composition are less than about 0.5 ppm as measured by GC/MS headspace analysis described in this disclosure.

Certain terms used throughout this disclosure are defined herein below so that the present invention may be more readily understood. Additional definitions are set forth throughout the disclosure.

Each term that is not explicitly defined in the present application is to be understood to have a meaning that is commonly accepted by those skilled in the art. If the construction of a term would render it meaningless or essentially meaningless in its context, the term's definition should be taken from a standard dictionary.

The use of numerical values in the various ranges specified herein, unless expressly indicated otherwise, are considered to be approximations as though the minimum and maximum values within the stated ranges were both preceded by the word "about." In this context, the term "about" is meant to encompass the stated value ±a deviation of 1%, 2%, 3%, 4%, or not more than 5% of the stated value. In this manner, slight variations above and below the stated ranges can be used to achieve substantially the same results as the values within the ranges. In addition, the disclosure of these ranges is intended as a continuous range including every value between the minimum and maximum values.

Unless otherwise indicated, % solids or weight % (wt %) are stated in reference to the total weight of a specific formulation, emulsion, or solution.

Unless otherwise indicated, the terms "polymer" and "thermoplastic resin" do not necessarily mean the same thing but include both homopolymers having the same recurring unit along the backbone, as well as copolymers having two or more different recurring units along the backbone. For instance, polymer refers to a molecule having a number averaged molecular weight of greater than 5,000 g/mol, as measured by GPC, whereas a "thermoplastic resin" refers to a molecule having a number average molecular weight of less than 5,000 g/mol, as measured by GPC.

Such polymers or thermoplastic resins include but are not limited to, materials prepared by either condensation, cationic, anionic, Ziegler-Natta, reversible addition-fragmentation chain-transfer (RAFT), or free radical polymerization. Further, the term "thermoplastic resin" or "starting thermoplastic resin" when used alone refers to the unmodified, or non-modified thermoplastic resin. Furthermore, while the term "polymer" is meant to encompass elastomers, the term "elastomer" does not necessarily encompass all polymers. In other words, as known to one of skill in the art, not all polymers are elastomers.

The term "comprising" (and its grammatical variations) as used herein is used in the inclusive sense of "having" or "including" and not in the exclusive sense of "consisting only of."

The terms "a" and "the" as used herein are understood to encompass one or more of the components, i.e., the plural as well as the singular.

The term "C5 thermoplastic resin" as used herein means aliphatic C5 hydrocarbon thermoplastic resins that are produced from the polymerization of monomers comprising C5 and/or C6 olefin species boiling in the range from about 20° C. to about 200° C. at atmospheric pressure. These monomers are typically generated from petroleum processing, e.g. cracking. The aliphatic C5 hydrocarbon thermoplastic resins of this invention can be produced by any method known in the art. In one embodiment, aliphatic C5 hydrocarbon thermoplastic resins are prepared by cationic polymerization of a cracked petroleum feed containing C5 and C6 paraffins, olefins, and diolefins also referred to as "C5 monomers." These monomer streams are comprised of cationically polymerizable monomers such as 1,3-pentadiene which is the primary reactive component along with cyclopentene, pentene, 2-methyl-2-butene, 2-methyl-2-pentene, cyclopentadiene, and dicyclopentadiene. The polymerizations are catalyzed using Friedel-Crafts polymerization catalysts such as Lewis acids (e.g., boron trifluoride ($BF_3$), complexes of boron trifluoride, aluminum trichloride ($AlCl_3$), and alkyl aluminum chlorides). In addition to the reactive components, nonpolymerizable components in the feed include saturated hydrocarbons that are in some instances co-distilled with the unsaturated components such as pentane, cyclopentane, or 2-methylpentane. Solid acid catalysts can also be utilized to produce aliphatic C5 hydrocarbon thermoplastic resins. Aliphatic C5 hydrocarbon thermoplastic resins include non-hydrogenated, partially hydrogenated, or fully hydrogenated resins. Aliphatic C5 thermoplastic resins can be obtained as Piccotac® C5 and Eastotac® C5 H2 thermoplastic resins from Eastman Chemical Company (Kingsport, Tenn., US).

The term "C5/C9 thermoplastic resin" as used herein means an aliphatic/aromatic hydrocarbon C5/C9 thermoplastic resin that is produced from the polymerization of monomers comprising at least one unsaturated aromatic C8, C9, and/or C10 species boiling in the range from about 100° C. to about 300° C. at atmospheric pressure and at least one monomer comprising C5 and/or C6 olefin species boiling in the range from about 20° C. to about 200° C. at atmospheric pressure. In one embodiment, C5 and/or C6 species include paraffins, olefins, and diolefins also referred to as "C5 monomers." These monomer streams are comprised of cationically polymerizable monomers such as 1,3-pentadiene which is the primary reactive component along with cyclopentene, pentene, 2-methyl-2-butene, 2-methyl-2-pentene, cyclopentadiene, and dicyclopentadiene. In one embodiment, unsaturated aromatic C8, C9, and/or C10 monomers are derived from petroleum distillates resulting from naphtha cracking and are referred to as "C9 monomers." These monomer streams are comprised of cationically polymerizable monomers such as styrene, alpha methyl styrene, beta-methyl styrene, vinyl toluene, indene, dicyclopentadiene, divinylbenzene, and other alkyl substituted derivatives of these components. The cationic polymerization is in some instances catalyzed using Friedel-Crafts polymerization catalysts such as Lewis acids (e.g., boron trifluoride ($BF_3$), complexes of boron trifluoride, aluminum trichloride ($AlCl_3$), and alkyl aluminum chlorides). Solid acid catalysts are also utilized to produce aliphatic/aromatic C5/C9 hydrocarbon thermoplastic resins. In addition to the reactive components, non-polymerizable components include, aromatic hydrocarbons such as xylene, ethyl benzene, cumene, ethyl toluene, indane, methylindane, naphthalene and other similar specifies. The non-polymerizable components of the feed stream are in some embodiments incorporated into the thermoplastic resins via alkylation reactions. Aliphatic/aromatic C5/C9 hydrocarbon thermoplastic resins include non-hydrogenated, partially hydrogenated resins, and hydrogenated resins. Aliphatic/aromatic C5/C9 thermoplastic resins can be obtained as Piccotac® thermoplastic resin from Eastman Chemical Company. The proportion of C5 to C9 is not limited. In other words, the amount of C5 monomer in the C5/C9 thermoplastic resin can be anywhere from 0.1 to 100% and vice versa the amount of C9 monomer in the C5/C9 thermoplastic resin can be from 0.1 to 100%.

The term "C9 thermoplastic resin" as used herein means an aromatic C9 hydrocarbon thermoplastic resin that is a thermoplastic resin produced from the polymerization of monomers comprising unsaturated aromatic C8, C9, and/or C10 species boiling in the range from about 100° C. to about 300° C. at atmospheric pressure. These monomers are typically generated from petroleum processing, e.g. cracking. The aromatic C9 hydrocarbon thermoplastic resins of this invention can be produced by any method known in the art. Aromatic C9 hydrocarbon thermoplastic resins are in one embodiment prepared by cationic polymerization of aromatic C8, C9, and/or C10 unsaturated monomers derived from petroleum distillates resulting from naphtha cracking and are referred to as "C9 monomers." These monomer streams are comprised of cationically polymerizable monomers such as styrene, alpha methyl styrene (AMS), beta-methyl styrene, vinyl toluene, indene, dicyclopentadiene, divinylbenzene, and other alkyl substituted derivatives of these components. Aliphatic olefin monomers with four to six carbon atoms are also present during polymerization in some embodiments of C9 resins. The polymerization is in some instances catalyzed using Friedel-Crafts polymerization catalysts such as Lewis acids (e.g., boron trifluoride ($BF_3$), complexes of boron trifluoride, aluminum trichloride ($AlCl_3$), and alkyl aluminum chlorides). In addition to the reactive components, nonpolymerizable components include, but are not limited to, aromatic hydrocarbons such as xylene, ethyl benzene, cumene, ethyl toluene, indane, methylindane, naphthalene, and other similar chemical species. The nonpolymerizable components of the feed stream are in some embodiments incorporated into the thermoplastic resins via alkylation reactions. C9 hydrocarbon thermoplastic resins include non-hydrogenated, partially hydrogenated, or fully hydrogenated resins. Aromatic C9 hydrocarbon thermoplastic resins can be obtained as Picco® C9 thermoplastic resin, and aliphatic hydrogenated and aliphatic/aromatic partially hydrogenated C9 H2 hydrocarbon thermoplastic resins can be obtained as Regalite® thermoplastic resin from Eastman Chemical Company.

The term "DCPD thermoplastic resin" as used herein means dicyclopentadiene (DCPD) thermoplastic resin, most commonly formed through ring opening metathesis polymerization (ROMP) of dicyclopentadiene in the presence of a strong acid catalyst, such as maleic acid or aqueous sulphuric acid, or thermal polymerization. Dicyclopentadiene is also formed in some embodiments by a Diels Alder reaction from two cyclopentadiene molecules and exists in two stereo-isomers: endo-DCPD and exo-DCPD. Typically, greater than 90% of the DCPD molecules present in commercial grades of DCPD are in the endo form. DCPD thermoplastic resins include aromatic-modified DCPD resins as well as hydrogenated, partially hydrogenated, and non-hydrogenated resins, though in most instances herein only H2 DCPD is described since it is the most readily commercially available form of DCPD. Aromatic-modified DCPD is also contemplated as a DCPD thermoplastic resin. Aromatic modification is, for instance, by way of C9 resin oil, styrene, or alpha methyl styrene (AMS), and the like. Hydrogenated and partially hydrogenated DCPD and hydrogenated and partially hydrogenated aromatic-modified DCPD resin is commercially available as Escorez® 5000-series resin (ExxonMobil Chemical Company, TX, US).

The term "IC thermoplastic resin" or "IC resin" as used herein means indene-coumarone (IC) thermoplastic resin, i.e. a synthetic thermoplastic terpene resin formed using feedstocks of indene and coumarone made from heavy-solvent naphtha obtained from the distillation of coal tar, which is a by-product of coke production. Heavy-solvent naphtha is rich in coumarone and indene, but most especially indene, and can be modified with phenol. These feedstocks can be formed by polymerization in $BF_3$ or $BF_3$ etherates. Catalysts can be removed by an alkaline wash or lime after polymerization. The resin can be isolated by steam distilling off the unreacted naphtha. IC thermoplastic resins can be used as plasticizers, and secure stress-strain properties at high levels. Examples of such resins include Novares® C indene-coumarone and Novares® CA phenol-modified indene-coumarone thermoplastic resin, which are commercially available from Rutgers Germany GmbH., Duisburg, Germany.

The term "PMR" as used herein means pure monomer thermoplastic resins. Pure monomer thermoplastic resins are produced from the polymerization of styrene-based monomers, such as, styrene, alpha-methyl styrene, vinyl toluene, and other alkyl substituted styrenes. Pure monomer thermoplastic resins are produced by any method known in the art. Pure monomer feedstock for the production of pure monomer thermoplastic resins are in some cases synthetically generated or highly purified monomer species. For example, styrene can be generated from ethyl benzene or alpha methyl styrene from cumene. In one embodiment, pure monomer hydrocarbon thermoplastic resins are prepared by cationic polymerization of styrene-based monomers such as styrene, alpha-methyl styrene, vinyl toluene, and other alkyl substituted styrenes using Friedel-Crafts polymerization catalysts such as Lewis acids (e.g., boron trifluoride ($BF_3$), complexes of boron trifluoride, aluminum trichloride ($AlCl_3$), and alkyl aluminum chlorides). Solid acid catalysts can also be utilized to produce pure monomer thermoplastic resins. The pure monomer thermoplastic resins disclosed herein are non-hydrogenated, partially hydrogenated, or fully hydrogenated resins. The term "hydrogenated" as used herein is also indicated alternatively in the shorthand "H2" and when H2 is used preceding or following a resin type it is intended to indicate that resin type is hydrogenated or partially hydrogenated, such as "PMR H2" and "C5 H2" for example.

When "H2" is used herein, "H2" is meant to encompass both fully hydrogenated resin samples and partially hydrogenated resin samples. Thus, "H2" refers to the condition in which the resin is either fully hydrogenated or at least partially hydrogenated. Pure monomer thermoplastic resins are in some instances obtained as Piccolastic® styrenic hydrocarbon thermoplastic resins, Kristalex® styrenic/alkyl styrenic hydrocarbon thermoplastic resins, Piccotex® alkyl styrenic hydrocarbon thermoplastic resins, and Regalrez® hydrogenated or partially hydrogenated pure monomer thermoplastic resins from Eastman Chemical Company (Kingsport, Tenn., US).

The term "terpene thermoplastic resin" or "polyterpene resin" as used herein means thermoplastic resins produced from at least one terpene monomer. For example, α-pinene, β-pinene, d-limonene, and dipentene can be polymerized in the presence of aluminum chloride to provide polyterpene thermoplastic resins. Other examples of polyterpene thermoplastic resins include Sylvares® TR 1100 and Sylvatraxx® 4125 terpene thermoplastic resin (AZ Chem Holdings, LP, Jacksonville, Fla., US), and Piccolyte® A125 terpene thermoplastic resin (Pinova, Inc., Brunswick, Ga., US). Terpene thermoplastic resins can also be modified with aromatic compounds. Sylvares® ZT 105LT and Sylvares® ZT 115 LT terpene thermoplastic resins are aromatically modified (Az Chem Holdings, LP, Jacksonville, Fla., US).

It is to be understood that encompassed by the above definitions of certain types of thermoplastic resins, such as DCPD, PMR, C5, C9, C5/C9, IC, terpene, and the like, including hydrogenated, partially-hydrogenated, and non-hydrogenated versions of these resins, that these thermoplastic resins include resins of similar types generated by mixing or blending of dissimilar feedstocks to produce heterogeneous mixtures of the feedstocks used to generate the thermoplastic resins. Furthermore, it is to be understood that at least with respect to the PMR and terpene thermoplastic resins discussed herein these thermoplastic resins encompass various known derivatives of such thermoplastic resins such as phenol-modified and rosin-modified versions of the resins.

"The initial calibration was performed by preparing solutions containing the individual components in methanol at concentrations ranging from 1-5000 parts per million. 10 μL of each solution was analyzed at 190° C. for 10 minutes, and from the resultant calibration curves, a table of relative response factors was generated. All subsequent calibrations were performed with cyclohexane and toluene, and specific components were quantified using response factors relative to either cyclohexane or toluene."

The term "volatile organic compound" (VOC) as used herein means volatile organic compounds that are measured according to head space gas spectrometry/mass chromatography (GC/MS). In this method, a headspace sampler is interfaced with a gas chromatograph equipped with a mass selective detector. The sample size is 0.1 grams of sample in a 22.5 ml headspace vial. Sampling conditioning temperatures are 100° C. for 30 minutes and 190° C. for 30 minutes. The initial calibration was performed by preparing solutions containing the individual components in methanol at concentrations ranging from 1-5000 parts per million. 10 μL of each solution was analyzed at 190° C. for 10 minutes, and from the resultant calibration curves, a table of relative response factors was generated. All subsequent calibrations were performed with cyclohexane and toluene, and specific components were quantified using response factors relative to either cyclohexane or toluene. Generally, the volatile organic compounds (VOCs) are compounds having a boiling/elution temperature range up to the boiling/elution temperature of compounds having 25 carbon atoms. In one embodiment, VOCs in tackifier compositions and adhesive compositions can include at least one selected from the group consisting of solvent compounds, monomers, comonomers, diluents, catalyst decomposition products, and decomposition products of the adhesive, which includes the base polymer, tackifier compositions, and additives.

The term "trace chemicals" refer to any volatile organic compounds that are of particular interest as odor causing compounds and health related concerns in adhesive formulations. Examples of trace chemicals include, but are not limited to, hexane, methyl chloride, tetrachloroethene, chloroform, trichloroethene, toluene, o, m, p-xylenes, ethylbenzene, styrene, cyclohexane, ethylcyclohexane, indene, vinyl toluene, and alpha methyl styrene.

The term "part by weight" in an adhesive formulation refers to parts of a component based on 100 parts of the adhesive formulation.

Thermoplastic hydrocarbon resins can be any that is known in the art. In one embodiment, thermoplastic hydrocarbon resins include, but are not limited to, PMR, DCPD, C5, C9, C5/C9, terpene, and IC thermoplastic resins, for example, as well as hydrogenated, partially-hydrogenated, and non-hydrogenated versions of these resins, and mixtures thereof.

The polymerization of thermoplastic resins from monomer units is typically performed in organic solvent according to known procedures in the art. The solvent is then removed by evaporation or other method after the polymerization process resulting in the thermoplastic hydrocarbon resin. During the evaporation process the solvent is selectively removed, however, some solvent and monomers remain in the thermoplastic hydrocarbon resin.

Improvement of such thermoplastic hydrocarbon resins is often desired to obtain more desirable physical properties in adhesive compositions. It has been surprisingly discovered that by removing a percentage of the volatile organic compounds (VOCs) from the thermoplastic hydrocarbon resin and the addition of an antioxidant composition comprising at least one primary antioxidant, optionally at least one secondary antioxidant, and at least one hindered amine light stabilizer (HALS) to the thermoplastic hydrocarbon resin, a tackifier composition is produced having low odor and low VOCs. This tackifier composition is useful in producing adhesives for consumer goods having low odor and low VOCs.

Any process known in the art can remove the volatile organic compounds from the thermoplastic hydrocarbon resins. To reduce the amount of VOCs in the thermoplastic hydrocarbon resins, several techniques known in the art are suitable, such as, but not limited to, one or more of: membrane separation, selective precipitation, selective polymerization conditions, evaporation and distillation, and preparative gel permeation chromatography.

Membrane separation is commonly employed as a purification technique in thermoplastic resin chemistry. (See, for instance, Bowen et al., *Chem. Eng. Res. Des.*, 76(8):885-893, 1998, and Llosa Tanco et al., *Process*, 4(29):1-21, 2016, herein incorporated by reference to the extent it does not contradict the statements in this disclosure). In this method, the membrane is typically a selective barrier that permits the separation of certain chemical species in a liquid by a combination of sieving and sorption diffusion mechanism. Membranes can selectively separate components of a liquid composition based on particle size, over a wide range of particle sizes and molecular weights, from large polymeric, i.e. greater than 5,000 g/mol Mn, to low monomolecular materials. Given this ability, membrane separation is a suitable technology to remove VOC fractions from thermoplastic hydrocarbon resins of many different types.

Selective precipitation is also suitable for removing VOC fractions from thermoplastic resins. (See, for example, Niederauer et al., *Bioseparation*, Vol. 47, "Advances in Biochemical Engineering/Biotechnology," pages 159 to 188, 2006; and Loadman, M. J. R., "Analysis of Rubber and Rubber-Like Polymers," 4$^{th}$ Ed., Springer Science and Business Media, B. V., Dordrecht, Netherlands, 1998). The solubility in a given solvent depends on its concentration, molecular weight, and the temperature of the solution. Under certain conditions, the thermoplastic hydrocarbon resin with a molecular weight above a certain value is not soluble anymore and precipitates, while the low molecular weight species remain soluble. By separating the precipitate from the solution by filtration or centrifuging, the VOC fractions can be removed from thermoplastic hydrocarbon resins.

Another technique commonly used to separate VOCs from thermoplastic resins is preparative gel permeation chromatography, sometimes referred to in the literature as size exclusion chromatography (SEC) or gel permeation chromatography. (See, for example, Lesec, J., J. *Liquid Chrom.*, 8(5):875-923, 2006; and Striegel, A. et al., "Modern Size-Exclusion Liquid Chromatography: Practice of Gel Permeation and Gel Filtration Chromatography," 2$^{nd}$ Ed., John Wiley & Sons, Inc., Hoboken, N.J., 2009, herein incorporated by reference to the extent it does not contradict the statements in this disclosure). This methodology is successfully applied in the pharmaceutical industry to separate and fractionate mixtures. As applied to thermoplastic resin samples, a solution of the thermoplastic hydrocarbon resin sample is applied to the top of a gel column. The gel particles have distinct pore sizes of a diameter that is in the same range of the thermoplastic hydrocarbon resin. The low molecular weight fraction of the thermoplastic hydrocarbon resin will diffuse deep into the gel particle pores, while the larger molecular weight fractions of the thermoplastic hydrocarbon resin can only diffuse a small distance into the gel. As a consequence, the larger sized molecules of the thermoplastic hydrocarbon resin are less retained then the smaller sized molecules, resulting in a separation between the VOC fraction of the thermoplastic hydrocarbon resin and larger thermoplastic hydrocarbon resin molecules.

Evaporation (wiped film evaporation) and distillation techniques are widely used to separate VOCs from hydrocarbon thermoplastic resins. (See, for instance, U.S. Pat. No. 4,160,692, herein incorporated by reference to the extent it does not contradict the statements in this disclosure). Temperature and pressure levels are selected to achieve adequate separation. In addition, the use of a carrier gas, such as a stream of nitrogen, or stream of steam, can help to improve the separation, but also specific designs of evaporation/distillation hardware, such as thin film evaporators, or distillation columns, can enhance the separation. Evaporation has typically a lower selectivity than distillation and is used when there is a large difference in boiling point between the distillate and residue.

In one embodiment of the invention, steam stripping is used to remove the VOCs from the thermoplastic hydrocarbon resin. Any process of steam stripping can be utilized. In one example, molten thermoplastic hydrocarbon resin and steam are fed to a counter current contacting device. Steam and VOCs exit near or at the top as a vapor stream which is condensed and may be decanted. The remaining molten resin exits near or at the base as product. The contacting device may have packing, or trays, or any other type vapor-liquid contacting internals. The contactor is operated under vacuum at about 10 to about 1000 mbar, or from about 3 to about 100 mbar, or from about 30 to about 50 mbar. The temperature in the column is from about 180 to about 280° C., or from about 190 to about 260° C., or from about 190 to about 220° C. The steam flow can be from about 0.5% to about 5% or from about 2% to about 5% by weight based on the flowrate of the molten thermoplastic hydrocarbon resin. The temperature, steam flow, and vacuum can all be adjusted to produce the desired softening point and VOC removal. Higher pressure can require more steam and/or higher temperature.

In another embodiment of the invention, a rotary film evaporator is utilized to remove VOCs from the thermoplastic hydrocarbon resin. The temperature of the rotary film evaporator is generally less than 240° C.

The antioxidant composition comprises at least one primary antioxidant, optionally at least one secondary antioxidant, and at least one hindered amine light stabilizer (HALS). The primary antioxidant, secondary antioxidant, and HALS can be added in portions or all at once to the thermoplastic hydrocarbon resin at any time after the resin is polymerized or after hydrogenated. The antioxidants can also be added after a portion or all of the VOCs are removed. The primary antioxidant, optionally secondary antioxidant, and HALS can be added all at once or in increments.

The primary antioxidant can be any that is known in the art. In one embodiment, the primary antioxidant is at least one sterically hindered phenol selected from the group consisting of CI-CXIX:

C-(I)

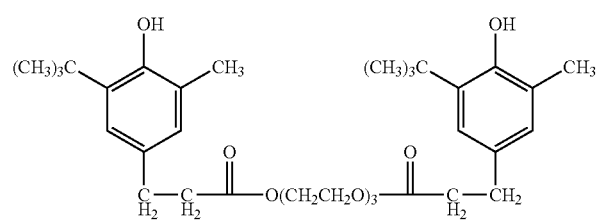

-continued
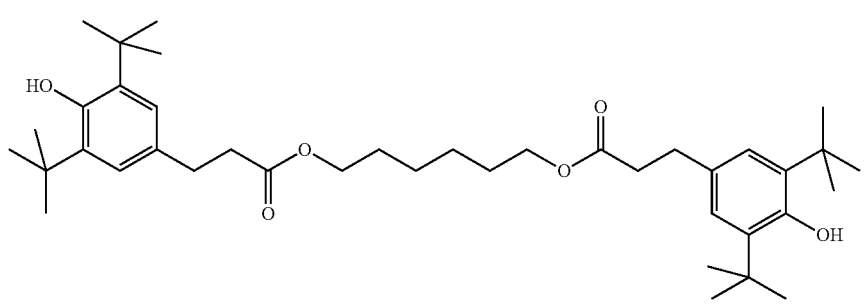
C-(II)
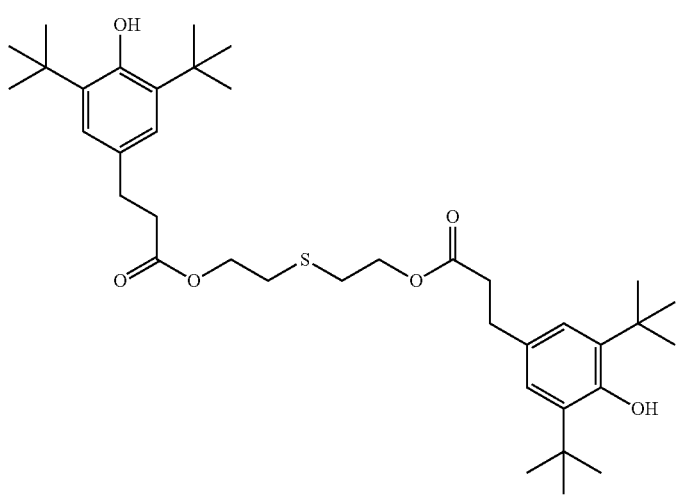
C-(III)
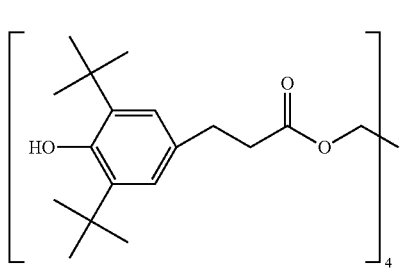
C-(IV)
wherein R=$C_8H_{17}$ or $C_{18}H_{37}$
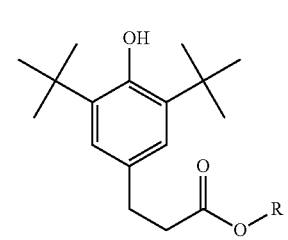
C-(V)
-continued
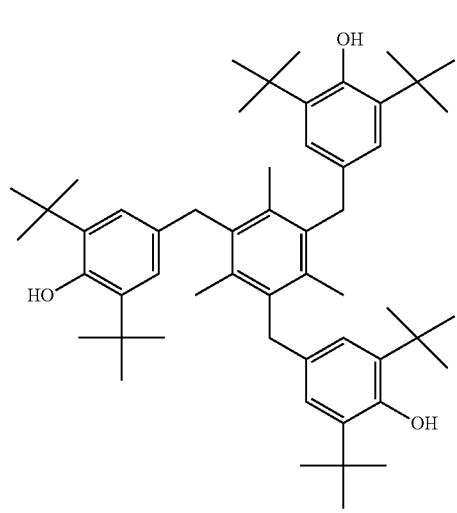
C-(VI)
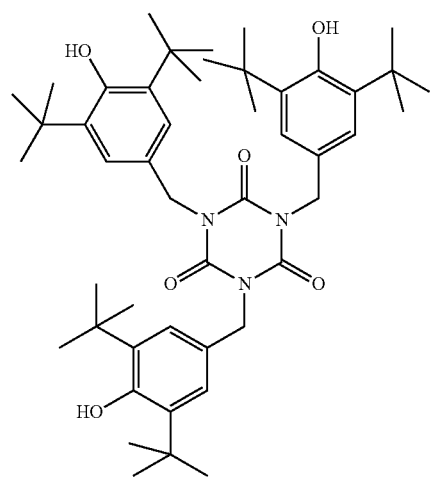
C-(VII)

C-(VIII)
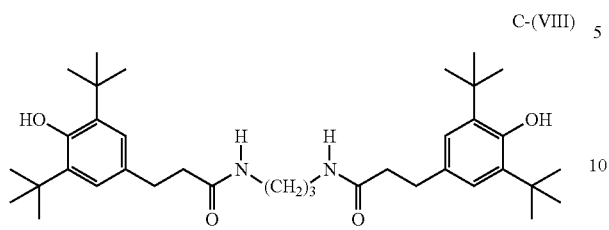
C-(IX)
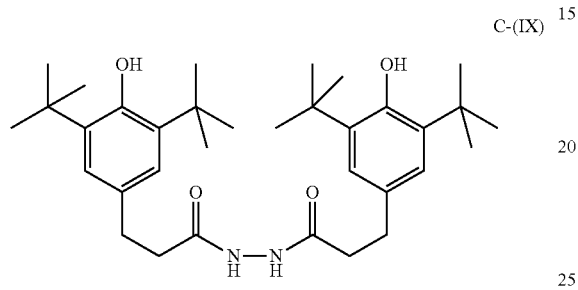
C(X)
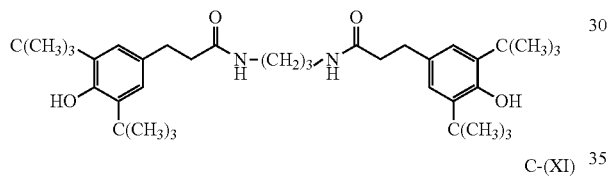
C-(XI)
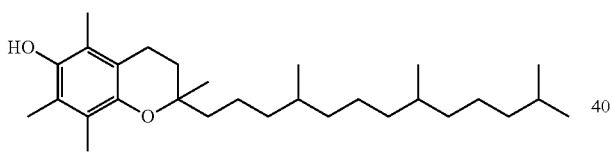
C-(XII)
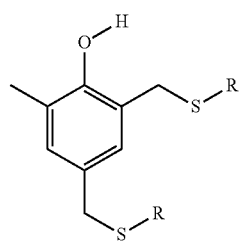
wherein R=$C_8H_{17}$ or $C_{12}H_{25}$;
C-(XIII)
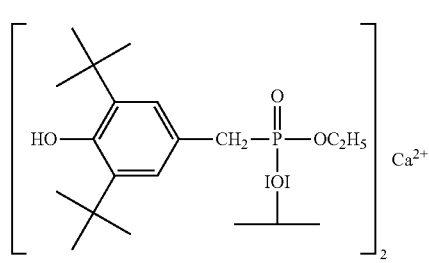
C(XIV)
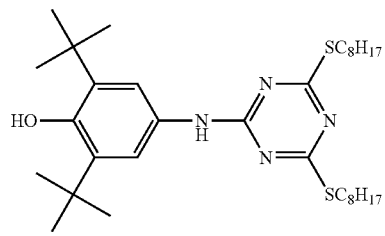
C-(XV)
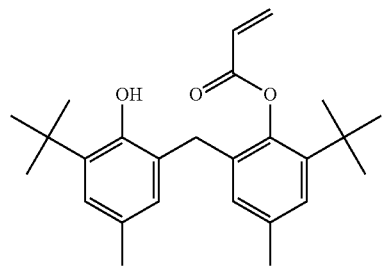
C-(XVI)
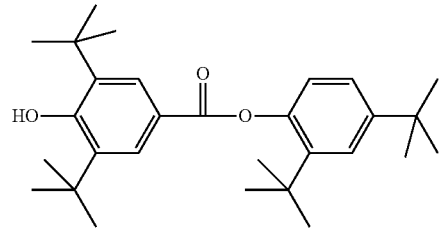
C-(XVII)
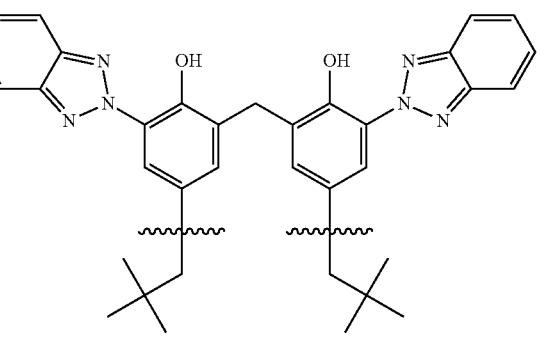
C-(XVIII)
C-(XIX)
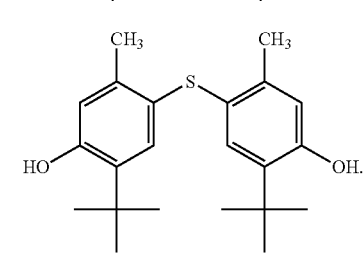
Secondary arylamines, another type of primary antioxidant, are more reactive toward oxygen centered radicals than are hindered phenols. Synergism between secondary arylamines and hindered phenols leads to regeneration of the amine from the reaction with the phenol. An example of a secondary arylamine antioxidant isbenzenamine, N-phenyl-, reaction products with 2,4,4-trimethylpentene (CAS 68411-46-1), that can be obtained from BASF as Irganox 5057®.

The secondary antioxidant can be any that is known in the art. In one embodiment, the secondary antioxidant is an organo-phosphite, thioether (or organic sulfide), or hydroxyl-amine.

Examples of organo-phosphite antioxidants include, but are not limited to, 2, 2',T-Nitrilo[triethyl-25 tris[3,3,5,5-tetra-tert.-butyl-1,1-biphenyl-2,2diyl] phosphite (CAS 80410-33-9); Bis(2,4-di-tert.-butyl-6-methylphenyl)-ethylphosphite (CAS 145650-60-8); Bis-(2,4-ditert.-butylphenol) pentaerythritol diphosphate (CAS 26741-53-7); Tris(2,4-di-tert.butylphenyl) phosphite (CAS 31570-04-4); Tetrakis(2,4-di-tert-butylphenyl)[1, 1-biphenyl]-4,4'-diylbisphosphonite (CAS 119345-01-6); and Tri-(nonylphenol)-phosphite 30.

These phosphite antioxidants can be obtained as Irgafos® 12, Irgafos® 38, Irgafos® 126, Irgafos® 168, Irgafos®, and Irgafos® antioxidants from BASF.

Examples of thioether antioxidants are Didodecyl-3,3'-thiodipropionate (CAS 123-28-4), 3,3'-Thiodipropionic acid dioctadecylester (CAS 693-36-7). These thioether antioxidants can be obtained as Irganox® PS 800 and Irgafos® 802 from BASF.

An example of a hydroxyl-amine based antioxidant is oxidized bis(hydrogenated tallow alkyl) amines (CAS: 143925-92-2) which can be obtained as Irgastab® FS 042 from BASF.

The hindered amine light stabilizer (HALS) can be any that is known in the art. In one embodiment, the HALs compound is at least one selected from the group consisting of A(1)-A(X):

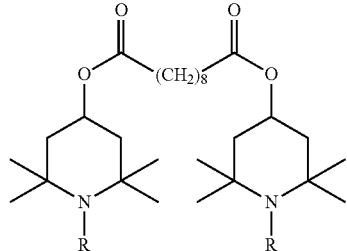

A-(I)

wherein R=H, CH$_3$ or OC$_8$H$_{17}$

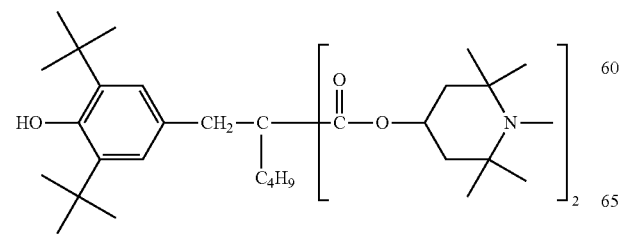

A-(II)

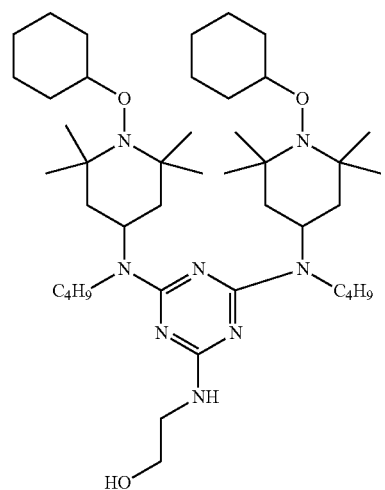

A-(III)

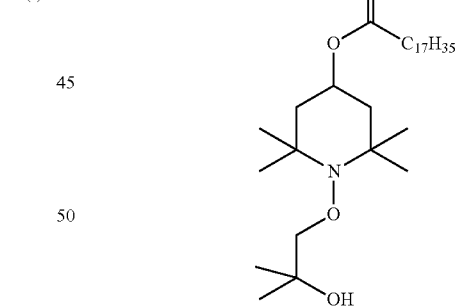

A-(IV)

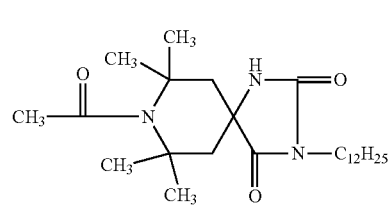

A-(V)

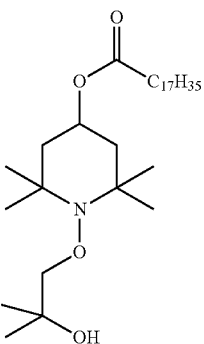

A-(VI)

A(VII)

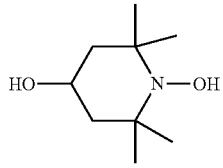

A-(VIII)

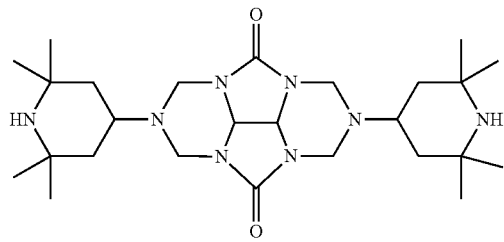

A-(IX)

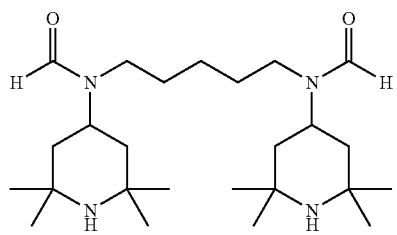

A-(X)

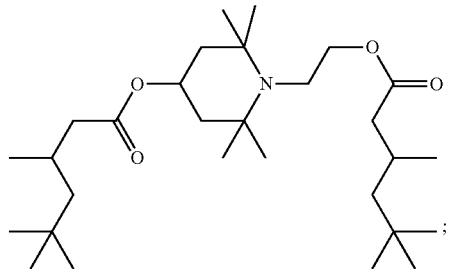

The amount of primary antioxidant can range from about 0.1% to about 1%, from about 0.1% to about 0.9%, from about 0.1% to about 0.8%, from about 0.1% to about 0.7%, from about 0.3% to about 0.6% from about 0.3% to about 0.5% by weight based on the weight of the thermoplastic hydrocarbon resin.

The amount of secondary antioxidant can range from about 0.1% to about 1%, from about 0.1% to about 0.9%, from about 0.1% to about 0.8%, from about 0.1% to about 0.7%, from about 0.3% to about 0.6% from about 0.3% to about 0.5% by weight based on the weight of the thermoplastic hydrocarbon resin.

The amount of HALS can range from about 0.05% to about 0.5%, from about 0.05% to about 0.45%, from about 0.05% to about 0.4%, from about 0.05% to about 0.35%, from about 0.05% to about 0.3%, from about 0.05% to about 0.25%, from about 0.05% to about 0.2%, from about 0.05% to about 0.15%, from about 0.05% to about 0.1% by weight based on the weight of the thermoplastic hydrocarbon resin.

In one embodiment, the antioxidant composition comprises the compounds shown in Table 1.

TABLE 1

| Name | Irganox ® 1010 (primary antioxidant) | Tinuvin ® 770 (HALS) |
| --- | --- | --- |
| CAS # | 6683-19-8 | 52829-07-9 |
| Structure | *(structure shown)* | *(structure shown)* |
| Molecular weight | 1178 g/mol | 481 g/mol |
| Chemical name | Pentaerythritol tetrakis(3-(3,5-di-tert-butyl-4-hydroxyphenyl)propionate) | Bis(2,2,6,6,-tetramethyl-4-piperidyl)sebaceate |
| Type/Category | Primary antioxidant (Sterically) hindered phenolic antioxidant | Hindered amine light stabilizer (HALS) Hindered amine stabilizer (HALS) |
| Trade Names | Irganox ® 1010 (BASF) SONGNOX ® 1010 (Songwon) BNX ® 1010 (Mayzo) | Tinuvin ® 770 (BASF) SABO ® STAB UV 70 (Songwon) BLS ® 1770 (Mayzo) |
| Amount | From about 0.1% to 1 wt % based on the amount of thermoplastic hydrocarbon resin | From about 0.05% to about 0.5 wt % based on the amount of thermoplastic hydrocarbon resin |

In another embodiment, the antioxidant composition comprises the compounds shown in Table 2.

TABLE 2

| Name | Irganox ® 1010 (primary antioxidant) | Irgafos ® 168 (secondary antioxidant) | Tinuvin ® 770 (HALS) |
|---|---|---|---|
| CAS # | 6683-19-8 | 31570-04-4 | 52829-07-9 |
| Structure | [structure: HO-phenyl(di-tert-butyl)-(CH$_2$)$_2$-C(=O)-O-CH$_2$-]$_4$-C | [di-tert-butylphenyl-O]$_3$-P | HN-(tetramethylpiperidyl)-OC(CH$_2$)$_8$CO-(tetramethylpiperidyl)-NH |
| Molecular weight | 1178 g/mol | 646.9 g/mol | 481 g/mol |
| Chemical name | Pentaerythritol tetrakis(3-(3,5-di-tert-butyl-4-hydroxyphenyl)propionate) | Tris(2,4-ditert-butylphenyl)phosphite | Bis(2,2,6,6,-tetramethyl-4-piperidyl)sebaceate |
| Type/Category | Primary antioxidant (Sterically) hindered phenolic antioxidant | Secondary antioxidant phosphite processing stabilizer | Hindered amine light stabilizer (HALS) Hindered amine stabilizer (HALS) |
| Trade Names | Irganox ® 1010 (BASF) SONGNOX ® 1010 (Songwon) BNX ® 1010 (Mayzo) | Irgafos ® 168 (BASF) Songnox ® 1680 (Songwon) Benefos ® 1680 (Mayzo) | Tinuvin ® 770 (BASF) SABO ® STAB UV 70 (Songwon) BLS ® 1770 (Mayzo) |
| Amount | From about 0.1% to 1 wt % based on the amount of thermoplastic hydrocarbon resin | From about 0.1% to 1 wt % based on the amount of thermoplastic hydrocarbon resin | From about 0.05% to about 0.5 wt % based on the amount of thermoplastic hydrocarbon resin |

The tackifier composition of this invention can be utilized in any adhesive composition known in the art. Generally, an adhesive composition comprises a base polymer and a tackifier composition. Other additives to adhesive compositions include, but are not limited to, waxes, oils, plasticizers, and other compounds.

In the composition embodiments described herein, the adhesive compositions can comprise at least 1, 2, 3, 4, 5, 10, 15, 20, 25, 30, 35, 40, 45, 50, 55, or 60 and/or not more than 99, 95, 90, 85, 80, 75, 70, or 65 weight percent of at least one tackifier composition based on the weight of the adhesive composition.

In various embodiments, the adhesive compositions comprise 10, 20, 30, or 40 and/or not more than 90, 80, 70, or 55 weight percent of at least one base polymer component based on the weight of the adhesive composition.

The adhesive compositions disclosed herein, in various embodiments, contain a base polymer, a tackifier composition, and other additives such as, but not limited to, oils, waxes, plasticizers, antioxidants, and fillers, depending on the end use application.

Base polymers for adhesive compositions include polyolefins, styrene block copolymers, ethylene vinyl-acetate polymers, and olefinic polymers.

Any polyolefins (PO) known in the art for use in adhesives can be utilized in this invention. In one embodiment, the polyolefin can be selected from the group consisting of linear low density polyethylene (LDPE) high density polyethylene (HDPE), atactic polypropylene (PP or APP), polybutene-1, and oxidized polyethylene). HDPE has higher melting point and better temperature resistance). Atactic polypropylene (PP or APP), polybutene-1, oxidized polyethylene, etc. can provide very good adhesion to polypropylene, good moisture barrier, chemical resistance against polar solvents and solutions of acids, bases, and alcohols. Polyolefins have low surface energy and provide good wetting of most metals and polymers. Polyolefins made by metallocene catalyzed synthesis have narrow distribution of molecular weight and correspondingly narrow melting temperature range. PE and APP are usually used on their own or with just a small amount of tackifiers (usually hydrocarbons) and waxes (usually paraffins or microcrystalline waxes). Polybutene-1 and its copolymers are soft and flexible, tough, partially crystalline, and slowly crystallizing with long open times. The low temperature of recrystallization allows for stress release during formation of the bond.

The styrenic block copolymers (SBC) used in adhesive compositions of the present invention is any styrene containing block copolymer or mixture thereof, including modified and/or hydrogenated derivatives thereof. Examples include, but are not limited to, SBS (styrene-butadiene-styrene), SIS (styrene-isoprene-styrene), SEBS (styrene-ethylene-butylene-styrene), SEPS (styrene-ethylene/propylene-styrene) block copolymers, SVS (styrene-vinylbutadiene-styrene), SB (styrene-butadiene diblock polymers), and SI (styrene-isoprene diblock polymers). In embodiments when hot melt adhesives are produced, particular useful styrenic block copolymers are S—I-S block copolymers and S-B-S block copolymers. However, the present invention is not limited to these types of styrenic copolymers. Commercially available SBC polymers include, for example, those polymers manufactured under the trademarks "Kraton®" from Kraton, "Stereon®" from Firestone, "Europrene®" from Polimeri Europa (Former Polimeri Europa (EniChem), etc. Other suppliers are GoodYear, Lanxess, Zeon, and JSR.

Styrene block copolymers (SBC), also called styrene copolymer adhesives and rubber-based adhesives, have good low-temperature flexibility, high elongation, and high heat resistance. They are frequently used in pressure-sensitive adhesive applications, where the composition retains tack even when solidified; however non-pressure-sensitive formulations are also used. They usually have A-B-A structure, with an elastic rubber segment between two rigid plastic endblocks. The A-B-A structure promotes a phase separation of the polymer, binding together the end blocks, with the central elastic parts acting as cross-links; thus SBCs do not require additional cross-linking. Styrene-butadiene-styrene (SBS) polymers are used in high-strength PSA applications. Styrene-isoprene-styrene (SIS) polymers are used in low-viscosity high-tack PSA applications. Styrene-ethylene/butylene-styrene (SEBS) are used in low self-adhering nonwoven applications.

Olefinic polymers can also be used in adhesives formulations, including hot melt adhesives. Olefinic polymers include ethylene vinyl acetate (EVA), amorphous polyolefins, metallocene polyolefins, and olefin block copolymers.

Ethylene vinyl-acetate (EVA) is a solid, transparent, flexible ethylene vinyl aetate copolymer. It is normally categorized by percent vinyl acetate (VA) content and melt flow rate (MFR) or melt index (MI). Most commonly used EVAs contain between about 19% and about 28% VA by weight. The MI values can range from about 3 to about 2500. EVA polymers are sold under trade names Elvax® from DOW Chemical (former DuPont), Ateva® from Celanese corporation, Nipoflex® from Tosoh, and Greenflex® from Distrupol, etc.

Amorphous polyolefin (APO) polymers are compatible with many solvents, tackifiers, waxes, and polymers; they find wide use in many adhesive applications. APO hot melt adhesives have good fuel and acid resistance, moderate heat resistance, are tacky, soft and flexible, have good adhesion and longer open times than crystalline polyolefins. APOs tend to have lower melt viscosity, better adhesion, longer open times and slow set times than comparable EVAs. Some APOs can be used alone, but often they are compounded with tackifiers, waxes, and plasticizers (e.g., mineral oil, polybutene oil). Examples of APOs include, but are not limited to, amorphous (atactic) propylene (APP), amorphous propylene/ethylene (APE), amorphous propylene/butene (APB), amorphous propylene/hexene (APH), amorphous propylene/ethylene/butene.

Amorphous polypropylene (APP) was first produced as a by-product of crystalline polypropylene and was obtained by solvent extraction. This APP polymer could be combined with various tackifiers, plasticizers, waxes, etc. to produce an adhesive that can be used for diaper construction, for example. Amorphous poly alpha olefins (APAOs) were produced on purpose using Ziegler-Natta catalysis and can be made using a variety of monomers, including, but not limited to, propylene, ethylene and butene. Various copolymers and terpolymers are produced by a number of manufacturers. They include Evonik Industries, who produce the Vestoplast® polymers; REXtac, LLC, who produces the Rextac® RT range of materials and Eastman Chemical, manufacturers of the Eastoflex® line of polymers. They are all characterized by having a low degree of crystallinity as measured by DSC. As commercially produced, they are random polymers having broad molecular weight distributions.

Metallocene polyolefins, also called polyolefin elastomers, can also be used as a base polymer in adhesive compositions. These polymers are made with metallocene catalysis technology. Polymers can be made using comonomer, such as butene-1 and octene-1, to produce polymers with very low levels of crystallinity (about 16~about 18%) and density of about 0.87 g/cm$^3$. Examples of these metallocene polymers include Affinity® and Engage® polymers from Dow Chemical Company, L-MODU® from Idemitsu (Japan). Metallocene polyolefin polymers are also supplied by several other companies, such as ExxonMobil Corporation (U.S.), LyondellBasel Industries Holdings B. V. (Netherlands), Chevron Phillips Chemical Company LLC (U.S.), Total SA (France), SABIC (Saudi Arabia), Japan Polychem Corporation Ltd, Braskem AG (Brazil), LG Chem Ltd. (South Korea), and others.

Olefin block copolymers (OBC) is a new class of polyolefin polymer produced using a chain shuttling catalysis technology that produces a linear block structure of the monomers rather than a random polymer produced by Ziegler-Natta or traditional metallocene technology. OBCs are manufactured by Dow Chemical under the trade name of Infuse®. OBCs consist of crystallizable ethylene-octene blocks (hard) and amorphous ethylene-octene blocks (soft). The block structures give the polymer much better elevated temperature resistance and elasticity compared to a typical metallocene random polymer of similar density. While some of the grades of Infuse® have low heat of fusion (approximately 20 Joules/gram) they would not be considered to be amorphous poly-alpha-olefins because the polymer architecture is completely different (i.e. block vs. random) and is specifically produced to have crystalline regions. Not only are they different on a structural basis, they are very different from a physical property standpoint with the OBCs having better elastic recovery, compression set and elevated temperature resistance. As such, they are sold into different markets for different end uses and are not considered equivalent for one another.

Exemplary base polymer components of the disclosed compositions include, but are not limited to, ethylene vinyl acetate copolymer, ethylene n-butyl acrylate copolymer, ethylene methyl acrylate copolymer, polyester, neoprene, acrylics, urethane, poly(acrylate), ethylene acrylic acid copolymer, polyether ether ketone, polyamide, styrenic block copolymers, random styrenic copolymers, hydrogenated styrenic block copolymers, styrene butadiene copolymers, natural rubber, polyisoprene, polyisobutylene, atactic polypropylene, polyethylene including atactic polypropylene, ethylene-propylene polymers, propylene-hexene polymers, ethylene-butene polymers, ethylene octene polymers, propylene-butene polymers, propylene-octene polymers, metallocene-catalyzed polypropylene polymers, metallocene-catalyzed polyethylene polymers, ethylene-propylene-butylene terpolymers, copolymers produced from propylene, ethylene, and various C4-C10 alpha-olefin monomers, polypropylene polymers, functional polymers such as maleated polyolefins, butyl rubber, polyester copolymers, copolyester polymers, isoprene, the terpolymer formed from the monomers ethylene, propylene, and a bicyclic olefin (known as "EPDM"), isoprene-based block copolymers, butadiene-based block copolymers, acrylate copolymers such as ethylene acrylic acid copolymer, butadiene acrylonitrile rubber, and/or polyvinyl acetate.

In another embodiment, adhesive formulations utilize polymers with low amounts of VOCs. Polyolefin polymers can have low VOC content and can assist in producing adhesives with low VOC and odor.

Waxes can also be contained in adhesive compositions. Any wax known in the art for use in adhesives can be utilized. Waxes, e.g. microcrystalline waxes, fatty amide waxes or oxidized Fischer-Tropsch waxes, increase the setting rate. One of the key components of adhesive formulations, waxes lower the melt viscosity and can improve bond strength and temperature resistance.

Various waxes also may be present in the adhesive composition of the present invention in amounts of about 0 to about 50 parts by weight based on the weight of the adhesive composition.

Low molecular weight polyethylene or polypropylene waxes, other than those polymerized by metallocene catalysts, are low molecular weight polymers made by direct polymerization of ethylene and propylene under conditions whereby molecular weight is controlled. These polymer waxes are available from a number of sources; polymer waxes useful in the hot melt adhesive compositions of the invention include Marcus® 200, 300, 500, 4040, and 2000 waxes from Marcus Oil and Chemical Corp. of Houston, Tex.; BARECO® C-4040 wax from Baker Hughes of Barnsdall, Okla.; and EPOLENE® C-10, C-18, and N-15 from Westlake Chemical Corp. of Houston, Tex.

Petroleum waxes, such as paraffin wax and microcrystalline wax, can also be utilized. Paraffin waxes are hydrocarbon mixtures with the general formula $C_nH_{2n+2}$ wherein $20 \leq n \leq 40$. Straight chain saturated hydrocarbons are the predominant functionality, though there are typically small amounts of unsaturated and/or branched hydrocarbons. Paraffin waxes are available from a broad range of sources including consumer sources.

Synthetic waxes made by polymerizing carbon monoxide and hydrogen, such as Fischer-Tropsch wax, can also be used in adhesive compositions. Fischer-Tropsch waxes are synthetic waxes produced by the Fischer-Tropsch process, which is a method for the synthesis of hydrocarbons and other aliphatic compounds from a mixture of hydrogen and carbon monoxide in the presence of a catalyst. The gaseous mixture can be obtained by coal gasification or natural gas reforming. The waxes are fractionated by chain length and are characterized as substantially saturated and linear aliphatic chains free of aromatic, sulfurous, and nitrogenous content. Fischer-Tropsch waxes are available from a number of sources. Some Fischer-Tropsch waxes useful in the hot melt adhesive compositions of the invention include those marketed under the trade name SASOLWAX®, for example SASOLWAX® C 80 and SASOLWAX® H 1, available from Sasol Wax North America Corp. of Hayward, Calif.; those marketed under the trade name VESTOWAX® available from Evonik Degussa of Essen, Germany; and those marketed under the trade name ACUMIST® available from Honeywell International Inc. of Morristown, N.J.

A product modified from above mentioned waxes can also be utilized. For example, maleic anhydride modified waxes from Honeywell: A-C 573A, A-C 573P, can be used.

As noted above, in some embodiments, the described compositions comprise additives particularly suitable for a specific end-use application. For example, if the adhesive is intended to serve as a hot melt packaging adhesive, as noted above, then in this embodiment, the composition will further comprise a wax. In some embodiments, the adhesive composition comprises at least 1, 2, 5, 8, or 10 and/or not more than 40, 30, 25, or 20 weight percent of at least one wax. In another embodiment, the compositions described herein comprise about 1 to about 40, about 5 to about 30, about 8 to about 25, or about 10 to about 20 weight percent of at least one wax. In such embodiments, a wax is included in the composition in an amount of between about 10 and about 100 parts wax per 100 parts of the adhesive composition.

In one embodiment of the invention, waxes containing low amounts of VOCs are utilized in the adhesive formulations. In one embodiment of the invention, the wax contains less than 0.5 ppm VOC as measured by headspace MS/GC analysis as specified in this disclosure.

Other additional stabilizers or antioxidants known in the art may also be present in the adhesive composition. In one embodiment of the invention, the additional antioxidant is a sterically hindered phenol compounds, such as Irganox° 1010 antioxidant obtained from BASF.

In other embodiments, the tackifier compositions that incorporate one or more thermoplastic hydrocarbon resin can further comprise at least about 0.1, 0.5, 1, 2, or about 3 and/or not more than about 20, 10, 8, or about 5 weight percent of at least one other antioxidant. Any antioxidant known to a person of ordinary skill in the art may be used in the adhesion compositions disclosed herein. Non-limiting examples of suitable other antioxidants include amine-based antioxidants such as alkyl diphenyl amines, phenyl-naphthylamine, alkyl or aralkyl substituted phenyl-naphthylamine, alkylated p-phenylene diamines, tetramethyl-diaminodiphenylamine and the like; and hindered phenol compounds such as 2,6-di-t-butyl-4-methylphenol; 1,3,5-trimethyl-2,4,6-tris (3',5'-di-t-butyl-4'-hydroxybenzyl)benzene; tetra kis [(methylene(3,5-di-t-butyl-4-hydroxyhydrocinnamate)] methane, such as IRGANOX® 1010 (BASF Corp., LA, US); octadecyl-3,5-di-t-butyl-4-hydroxycinnamate, such as IRGANOX® 1076 (BASF Corp., LA, US) and combinations thereof. Where used, the amount of the other antioxidant in the composition can be from about greater than 0 to about 1 wt %, from about 0.05 to about 0.75 wt %, or from about 0.1 to about 0.5 wt % of the total weight of the adhesive composition. In another such embodiment, the adhesive compositions comprise about 0.1 to about 20, about 1 to about 10, about 2 to about 8, or about 3 to about 5 weight percent of at least one other antioxidant.

Variety of fillers can be used in hot melt adhesive formulations. Fillers can have a deep effect on cost, compounding characteristics, and final adhesive properties. Any filler known in the art to be used in adhesive compositions can be utilized. The commonly used fillers include including calcium carbonate, carbon black, titanium oxide, zinc oxide, alumina trihydrate, barium sulfate, silica and kaolin clay. In another embodiment of the described compositions, the compositions comprise at least about 10, 20, 30, or about 40 and/or not more than about 90, 80, 70, or about 55 weight percent of at least one filler. In a further embodiment, the compositions comprise about 1 to about 90, about 20 to about 80, about 30 to about 70, or about 40 to about 55 weight percent of at least one filler.

Plasticizers can also be contained in adhesive compositions. Plasticizers can be any that is known in the art. Plasticizers include, but are not limited to, benzoates, such as, 1,4-cyclohexane dimethanol dibenzoate, glyceryl tribenzoate, or pentaerythritol tetrabenzoate, phthalates, oils, polyisobutylene, chlorinated paraffins, and the like.

Various plasticizing oils or extending oils also may be present in the adhesive composition of the present invention in amounts of about 0 to about 50 parts by weight. Commercially available plasticizing oils include, for example, those manufactured under the trademarks, "Shellflex®", "Ondina®" (both produced by Shell Chemical Company), "Primol®", "Flexon®" (Exxon Chemical Company), Hydrobrite® from Sonneborn or "Kaydol®" (Witco Chemical Company).

The plasticizing oils include not only the usual plasticizing oils, but also naphthenic/paraffinic oils, olefin oligomers and low molecular weight polymers, as well as vegetable and animal oil and derivatives of such oils. Plasticizer oils also include liquid resins as well as mixtures thereof with olefin oligomers and/or low molecular weight polymers. The examples of common plasticizing oils are Kaydol white mineral oil, Tufflo® mineral oil, Shellflex® 371N, Shelflex® 451, Calsol® 5550 Hydrobrite® 380 PO White Mineral Oil.

Liquid resin of use in this invention may be any resin having a R&B softening point below the R&B softening point of the tackifying resin of this invention. Preferably the liquid resin should have a R&B softening point below 50° C., most preferably, the liquid resin has e R&B softening point below ambient temperature (21° C.).

The oligomers may be polypropylenes, polybutenes, hydrogenated polyisoprene, hydrogenated butadiene, or the like having average molecular weights between about 350 Dalton and about 10,000 Dalton. Commercially available plasticizing oligomers include, for example, those manufactured under the trademarks, "Napvis®", "Hyvis®", which are both manufactured by BP Chemical Company, or "Amoco Polybutenes®", manufactured by the Amoco Chemical Specialities Company. Suitable vegetable and animal oils include glycerol esters of the usual fatty acids and polymerization products thereof.

In pressure sensitive adhesive (PSA) composition embodiments, such as adhesives used in tapes, mastics, and labels, and in nonwoven applications of the described adhesive compositions, various oils are added to the adhesive compositions. In one embodiment, the adhesive composition comprises at least about 1, 2, 5, 8, or about 10 and/or not more than about 40, 30, 25, or about 20 weight percent of at least one processing oil. In another embodiment of pressure sensitive adhesive compositions, the adhesive compositions comprise about 2 to about 40, about 5 to about 30, about 8 to about 25, or about 10 to about 20 weight percent of at least one processing oil. Processing oils include, but are not limited to, mineral oils, naphthenic oils, paraffinic oils, aromatic oils, castor oils, rape seed oil, triglyceride oils, and combinations thereof. Processing oils also include extender oils that are commonly used in various pressure-sensitive adhesive compositions. In another embodiment, the described adhesive composition comprises no processing oils.

In one embodiment of the invention, adhesive compositions utilize plasticizer oils having low VOC content. In some adhesive compositions, plasticizer oils having less than 0.5 ppm VOC based on headspace MS/GC analysis as defined in this disclosure.

In another embodiment of the compositions, one or more plasticizers are added to the adhesive compositions, such as, but not limited to, phthalate esters such as, for example, dibutyl phthalate and dioctyl phthalate, benzoates, terephthalates, and chlorinated paraffins. In one embodiment, the described adhesive compositions comprise at least about 0.5, 1, 2, or about 3 and/or not more than about 20, 10, 8, or about 5 weight percent of at least one plasticizer. In another embodiment, the adhesive compositions comprise about 0.5 to about 20, about 1 to about 10, about 2 to about 8, or about 3 to about 5 weight percent of at least one plasticizer. Other exemplary plasticizers include Benzoflex™ and Eastman 168™ (Eastman Chemical Company, Kingsport, Tenn., US).

In some embodiments, the compositions described herein include other conventional plastic additives in an amount that is sufficient to obtain a desired processing or performance property for the adhesive. The amount should not be wasteful of the additive nor detrimental to the processing or performance of the adhesive. Those skilled in the art of thermoplastics compounding, without undue experimentation but with reference to such treatises as Plastics Additives Database (2004) from Plastics Design Library (www.elsevier.com) can select from many different types of additives for inclusion into the compounds described herein. Non-limiting examples of optional additives include adhesion promoters; biocides (antibacterials, fungicides, and mildewcides), anti-fogging agents; anti-static agents; bonding, blowing and foaming agents; dispersants; fillers and extenders; fire and flame retardants and smoke suppressants; impact modifiers; initiators; lubricants; micas; pigments, colorants and dyes; oils and plasticizers; processing aids; release agents; silanes, titanates and zirconates; slip and anti-blocking agents; stabilizers (for example, Irganox® 1010 and Irganox® 1076, BASF Corporation, LA, US); stearates; ultraviolet light absorbers; viscosity regulators; waxes; and combinations thereof. Antioxidants are particularly useful for these compounds to provide additional durability.

Such compositions are manufactured in one embodiment by blending the base polymer and tackifier composition to form the adhesive. That is, the adhesive compositions described herein are in one embodiment prepared by combining the base polymer, tackifier composition and the additives using conventional techniques and equipment. As a non-limiting exemplary embodiment, the components of the compositions described herein are blended in a mixer such as a Sigma blade mixer, a plasticorder, a Brabender mixer, a twin-screw extruder, and/or an in-can blend can (pint-cans). In another embodiment, the compositions are shaped into a desired form, such as a tape or sheet, by an appropriate technique including, for example, extrusion, compression molding, calendaring, or roll coating techniques (gravure, reverse roll, and the like). In some embodiments, the compositions described herein are applied using curtain coating, slot-die coating, or sprayed through different nozzle configurations at different speeds using typical application equipment.

In another embodiment, the compositions described herein are applied to a substrate by melting the composition and then using conventional hot melt adhesive application equipment recognized in the art to coat the substrate with the composition. Substrates include, for example, textile, fabric, paper, glass, plastic, and metal materials. Typically, about 0.1 to about 100 g/m$^2$ of adhesive composition is applied to a substrate.

In one embodiment of this invention, a hot melt adhesive is provided comprising at least one base polymer and at least one tackifier composition; wherein the tackifier composition comprises at least one thermoplastic hydrocarbon resin and an antioxidant composition; wherein at least a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure. The hot melt adhesive can further comprise at least one selected from the group consisting of at least one oil, at least one wax, and at least one filler. The hot melt adhesive can also contain any additional antioxidant or stabilizer known in the art.

In an embodiment of the invention, a low odor and low VOC hot melt adhesive is provided. The hot melt adhesive composition comprises:
(a) About 5 parts to about 90 parts by weight of at least one base polymer;
(b) About 5 parts to about 90 parts by weight of at least one tackifier composition; wherein the tackifier composition comprises at least one thermoplastic hydrocarbon resin and an antioxidant composition; wherein a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure;
(c) 0 to about 50 parts by weight of at least one plasticizer;
(d) 0 to about 50 parts by weight of at least one wax;
(e) 0 to about 1 part by weight of at least one additional antioxidant; and
(f) 0 to about 80 parts by weight of at least one filler.

In an embodiment of the invention, a low odor and low VOC packaging adhesive composition is provided. The packaging hot melt adhesive composition comprises:
(a) about 50 to about 90 parts by weight of at least one EVA polymer;
(b) about 10 to about 50 parts by weight of at least one tackifer composition; wherein the tackifier composition comprises at least one fully hydrogenated or partially hydrogenated C9 resin and an antioxidant composition; wherein a portion of the volatile organic compounds in the C9 resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure; and
(c) 0 to about 1 part by weight of an additional antioxidant.

In an embodiment of the invention, a low odor and low VOC packaging adhesive is provided. The packaging hot melt adhesive comprises:
(a) about 10 to about 50 parts by weight of at least one EVA polymer;
(b) about 10 to about 50 parts by weight of at least one tackifer composition; wherein the tackifier composition comprises at least one fully hydrogenated or partially hydrogenated C9 resin and an antioxidant composition; wherein a portion of the volatile organic compounds in the C9 resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure;
(c) about 10 to about 50 parts by weight of at least one wax; and
(d) 0 to about 1 part by weight of at least one additional antioxidant.

In an embodiment of the invention, a low odor and low VOC packaging adhesive is provided. The packaging hot melt adhesive comprises:
(a) about 30 to about 80 parts by weight of at least one EVA polymer;
(b) about 10 to about 50 parts by weight of at least one tackifer composition; wherein the tackifier composition comprises at least one fully hydrogenated or partially hydrogenated C9 resin and an antioxidant composition; wherein a portion of the volatile organic compounds in the C9 resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure; and
(c) 0 to about 1 part by weight of at least one additional antioxidant.

In an embodiment of the invention, a low odor and low VOC packaging adhesive is provided. The packaging hot melt adhesive comprises:
(a) about 20 to about 90 parts by weight of at least one metallocene polymer;
(b) about 10 to about 50 parts by weight of at least one tackifer composition; wherein the tackifier composition comprises at least one fully hydrogenated or partially hydrogenated C9 resin and an antioxidant composition; wherein a portion of the volatile organic compounds in the C9 resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure;
(c) 0 to about 40 parts by weight of at least one plasticizing oil;
(d) 0 to about 40 parts by weight of at least one wax; and
(e) 0 to about 1 part by weight of at least one additional antioxidant.

In an embodiment of the invention, a low odor and low VOC packaging adhesive is provided. The packaging hot melt adhesive comprises:
(a) about 10 to about 50 parts by weight of at least one OBC polymer;
(b) about 30 to about 80 parts by weight of at least one tackifer compositions; wherein the tackifier composition comprises at least one fully hydrogenated or partially hydrogenated C9 resin and an antioxidant composition; wherein a portion of the volatile organic compounds in the C9 resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure;
(c) 0 to about 40 parts by weight of at least one oil;
(d) 0 to about 20 parts by weight of at least one wax; and
(e) 0 to about 1 part by weight of at least one antioxidant.

In an embodiment of the invention, a low odor and low VOC packaging adhesive is provided. The packaging hot melt adhesive comprises:

(a) about 40 to about 90 parts by weight of at least one APAO polymer;
(b) about 10 to about 50 parts by weight of at least one tackifier composition; wherein the tackifier composition comprises at least one fully hydrogenated or partially hydrogenated C9 resin and an antioxidant composition; wherein a portion of the volatile organic compounds in the C9 resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure;
(c) 0 to about 20 parts by weight of at least one oil;
(d) 0 to about 20 parts by weight of at least one wax; and
(e) about 0.2 to about 1 part by weight of at least one additional antioxidant.

In an embodiment of the invention, a low odor and low VOC hygiene adhesive is provided. The hygiene hot melt adhesive comprises:
(a) about 10 to about 40 parts by weight of at least one SBC copolymer;
(b) about 20 to about 80 parts by weight of at least one tackifier composition; wherein the tackifier composition comprises at least one fully hydrogenated or partially hydrogenated C9 resin and an antioxidant composition; wherein a portion of the volatile organic compounds in the C9 resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure;
(c) 0 to about 40 parts by weight of at least one oil; and
(d) 0 to about 1 part by weight of at least one additional antioxidant.

In an embodiment of the invention, a low odor and low VOC hygiene adhesive composition is provided. The hygiene hot melt adhesive composition comprises:
(a) about 10 to about 30 parts by weight of at least one SBC copolymer;
(b) about 50 to about 70 parts by weight of a tackifier composition; wherein the tackifier composition comprises at least thermoplastic hydrocarbon resin; wherein a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure;
(c) about 10 to about 30 parts by weight of at least one oil; and
(d) 0 to about 1 part by weight of at least one additional antioxidant.

In an embodiment of the invention, a low odor and low VOC hygiene adhesive is provided. The hygiene hot melt adhesive comprises:

(a) about 15 to about 25 parts by weight of at least one SBC copolymer;
(b) about 55 to about 65 parts by weight of at least one tackifier composition; wherein the tackifier composition comprises at least thermoplastic hydrocarbon resin; wherein a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure;
(c) about 15 to about 25 parts by weight of at least one oil; and
(d) 0 to about 1 part by weight of at least one additional antioxidant.

In an embodiment of the invention, a low odor and low VOC hygiene adhesive is provided. The hygiene hot melt adhesive comprises:
(a) about 20 to about 70 parts by weight of at least one SBC copolymer;
(b) about 20 to about 80 parts by weight of at least one tackifier composition; wherein the tackifier composition comprises at least thermoplastic hydrocarbon resin; wherein a portion of the volatile organic compounds in the thermoplastic hydrocarbon resin has been removed; wherein the antioxidant composition comprises at least one primary antioxidant, optionally at least one secondary antioxidant, and at least one HALS; wherein the levels of individual volatile organic compounds of interest in the tackifier composition are less than about 0.5 ppm as measured by GC/MS headspace analysis as described in this;
(c) 0 to about 40 parts by weight of at least one oil; and
(d) 0 to about 1 part by weight of at least one additional antioxidant.

In an embodiment of the invention, a low odor and low VOC hygiene adhesive is provided. The hygiene hot melt adhesive comprises:
(a) about 30 to about 50 parts by weight of at least one SBC copolymer;
(b) about 30 to about 50 parts by weight of at least one tackifier composition; wherein the tackifier composition comprises at least thermoplastic hydrocarbon resin; wherein a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure;
(c) about 10 to about 30 parts by weight of at least one oil; and
(d) 0 to about 1 part by weight of at least one additional antioxidant.

In an embodiment of the invention, a low odor and low VOC hygiene adhesive is provided. The hygiene hot melt adhesive comprises:
(a) about 20 to about 90 parts by weight of at least one metallocene polymer;
(b) about 10 to about 50 parts by weight of at least one tackifier composition; wherein the tackifier composition comprises at least thermoplastic hydrocarbon resin; wherein a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure;

(c) 0 to about 40 parts by weight of at least one oil;
(d) 0 about 40 parts by weight of at least one wax; and
(e) 0 to 1 part by weight of at least one additional antioxidant.

In an embodiment of the invention, a low odor and low VOC hygiene adhesive is provided. The hygiene hot melt adhesive comprises:

(a) about 10 to about 50 parts by weight of an OBC polymer;
(b) about 30 to about 80 parts by weight of at least one tackifier composition; wherein the tackifier composition comprises at least thermoplastic hydrocarbon resin; wherein a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure;
(c) 0 to about 40 parts by weight of at least one oil;
(d) 0 to about 20 parts by weight of at least one wax; and
(e) 0 to about 1 part by weight of at least one additional antioxidant.

In an embodiment of the invention, a low odor and low VOC hygiene adhesive is provided. The hygiene hot melt adhesive comprises:

(a) 40~90 parts by weight of at least one APAO polymer;
(b) 10~50 parts by weight of wherein the tackifier composition comprises at least thermoplastic hydrocarbon resin; wherein a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure;
(c) 0 to about 20 parts by weight of at least one oil;
(d) 0 to about 20 parts by weight of at least one wax; and
(e) 0 to about 1 part by weight of at least one additional antioxidant.

In another embodiment of the invention, a product assembly hot melt adhesive composition is provided. Product assembly adhesives are utilized to in the automobile industry, woodworking industries, and other applications. The product assembly hot melt adhesive composition comprises at least one base polymer, at least one tackifier composition, optionally at least one plasticizing oil, optionally at least one wax, optionally at least one filler, and optionally at least one additional antioxideant; wherein the tackifier composition comprises at least one thermoplastic hydrocarbon resin and an antioxidant composition; wherein a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure.

In another embodiment of the invention, the product assembly adhesive composition is provided comprising: a) about 5 parts to about 90 parts by weight of a base polymer; b) about 5 parts to about 90 parts by weight of at least one tackifier composition; wherein the tackifier composition comprises at least one thermoplastic hydrocarbon resin and an antioxidant composition; wherein a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure; c) 0 to about 50 parts by weight of at least one plasticizer oil, d) 0 to about 50 parts by weight of at least one wax, e) 0 to about 1 part by weight of at least one additional antioxidant; f) 0 to about 80 parts by weight of at least one organic or inorganic filler. The tackifier composition was previously described in this disclosure. The thermoplastic hydrocarbon resin can have a Rolling Ball softening point between about 70° C. and about 150° C.

In another embodiment of the invention, the product assembly adhesive composition is provided comprising: a) about 50 parts to about 90 parts by weight of at least one amorphous polyolefin; b) about 5 parts to about 90 parts by weight of at least one tackifier composition wherein the tackifier composition comprises at least one thermoplastic hydrocarbon resin and an antioxidant composition; wherein a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure; c) 0 to about 50 parts by weight of at least one plasticizer oil, d) 0 to about 50 parts by weight of at least one wax, e) 0 to about 1 part by weight of at least one additional antioxidant; f) 0 to about 80 parts by weight of at least one organic or inorganic filler. The tackifier composition was previously described in this disclosure. The thermoplastic hydrocarbon resin can have a Rolling Ball softening point between about 70° C. and about 150° C.

In another embodiment of the invention, the product assembly adhesive composition is provided comprising: a) about 50 parts to about 90 parts by weight of at least one amorphous polyolefin; b) about 5 parts to about 90 parts by weight of at least one tackifier composition wherein the tackifier composition comprises at least one thermoplastic hydrocarbon resin and an antioxidant composition; wherein a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure; c) 0 to about 50 parts by weight of at least one plasticizer oil, d) 0 to about 50 parts by weight of at least one wax, e) 0 to about 1 part by weight of at least one additional antioxidant; f) 0 to about 80 parts by weight of at least one organic or inorganic filler. The tackifier composition was previously described in this disclosure. The thermoplastic hydrocarbon resin can have a Rolling Ball softening point between about 70° C. and about 150° C.

In another embodiment of the invention, the automotive assembly adhesive composition is provided comprising: a) about 40 parts to about 90 parts by weight of at least one amorphous polyolefin; b) about 10 parts to about 50 parts by weight of at least one tackifier composition, wherein the tackifier composition comprises at least one thermoplastic hydrocarbon resin and an antioxidant composition; wherein a portion of the volatile organic compounds in the thermoplastic hydrocarbon resin has been removed; wherein the antioxidant composition comprises at least one primary antioxidant, optionally at least one secondary antioxidant, and at least one HALS; and wherein the levels of individual volatile organic compounds of interest in the tackifier composition are less than about 0.5 ppm as measured by GC/MS headspace analysis as described in this disclosure and wherein the thermoplastic hydrocarbon resin is a fully hydrogenated or partially hydrogenated C9; c) 0 to about 50 parts by weight of at least one plasticizer oil, d) 0 to about 50 parts by weight of at least one wax, e) 0 to about 1 part by weight of at least one additional antioxidant; f) 0 to about 80 parts by weight of at least one organic or inorganic filler. The tackifier composition was previously described in this disclosure. The thermoplastic hydrocarbon resin can have a Rolling Ball softening point between about 70° C. and about 150° C.

The invention has been described in detail with particular reference to preferred embodiments thereof, but it will be understood that variations and modifications can be affected within the spirit and scope of the invention.

EXAMPLES

This invention can be further illustrated by the following examples of preferred embodiments thereof, although it will be understood that these examples are included merely for purposes of illustration and are not intended to limit the scope of the invention unless otherwise specifically indicated.

Test Methods

Volatile organic compounds were measured according to head space gas spectrometry/mass chromatography (GC/MS). In this method, a headspace sampler is interfaced with a gas chromatograph equipped with a mass selective detector. The sample size is 0.1 grams of sample in a 22.5 ml headspace vial. Sampling conditioning temperatures are 100° C. for 30 minutes and 190° C. for 30 minutes. The initial calibration was performed by preparing solutions containing the individual components in methanol at concentrations ranging from 1-5000 parts per million. 10 μL of each solution was analyzed at 190° C. for 10 minutes, and from the resultant calibration curves, a table of relative response factors was generated. All subsequent calibrations were performed with cyclohexane and toluene, and specific components were quantified using response factors relative to either cyclohexane or toluene.

Example 1

VOC levels were determined for various commercial thermoplastic hydrocarbon resins as shown in the comparative examples in Table 3 as well as various inventive tackifier compositions comprising at least one thermoplastic hydrocarbon resin and the inventive antioxidant blends as shown in Table 4. The VOC levels were determined using the headspace MS/GC method described above at 190 C.° for 30 minutes.

TABLE 3

| | Comparative Samples | | | | | |
| --- | --- | --- | --- | --- | --- | --- |
| Samples | Comparative 1 | Comparative 2 | Comparative 3 | Comparative 4 | Comparative 5 | Comparative 6 |
| Stripping | No | Yes | No | No | No | No |
| Pentaerythritol tetrakis(3-(3,5-di-tert-butyl-4-hydroxyphenyl)propionate | — | — | 0.90% | 0.30% | 0.30% | 0.62% |
| Tris(2,4-ditert-butylphenyl)phosphite | — | — | — | — | — | 0.30% |
| Bis(2,2,6,6,-tetramethyl-4-piperidyl)sebaceate | — | — | 0.10% | — | — | 0.08% |
| | $C_9$-Partially hydrogenated | $C_9$-Partially hydrogenated | $C_9$-Partially hydrogenated | $C_9$-Partially hydrogenated | $C_9$-Fully hydrogenated | $C_9$-Partially hydrogenated |
| Methylene Chloride | ND | ND | ND | ND | ND | ND |
| Hexane | <0.2 | ND | ND | ND | ND | ND |
| Chloroform | ND | ND | ND | ND | ND | ND |
| Cyclohexane | 30.3 | 20.2 | 0.3 | 7.6 | 1.5 | 0.2 |
| Toluene | 9.4 | 5.1 | 0.7 | 3.5 | 0.2 | 2.4 |
| Ethylcyclohexane | 12.3 | 7.9 | <0.2 | 3.7 | 0.8 | <0.2 |
| Ethylbenzene | 8.7 | 5.6 | 0.9 | 2.2 | ND | 0.4 |
| P-Xylene | 2.5 | 1.4 | 0.37 | ND | ND | 0.2 |
| O-Xylene | ND | 0.6 | <0.2 | ND | ND | <0.2 |
| M-Xylene | ND | ND | ND | ND | ND | ND |
| Styrene | 30.2 | 20.0 | 3.52 | 8.1 | 0.6 | 1.9 |
| a-Methyl Styrene | 30.3 | 20.1 | 0.5 | 7.0 | ND | 0.3 |
| Vinyl Toluene | 13.9 | 8.5 | 1.03 | 2.5 | 0.3 | 0.9 |

TABLE 3-continued

Comparative Samples

| Samples | Comparative 1 | Comparative 2 | Comparative 3 | Comparative 4 | Comparative 5 | Comparative 6 |
|---|---|---|---|---|---|---|
| Indene | 123.2 | 89.8 | 13.54 | 17.2 | 2.7 | 12.7 |
| Tetrachloroethene | ND | ND | ND | ND | ND | ND |
| Trichloroethene | ND | ND | ND | ND | ND | ND |
| Total | 260.8 | 179.3 | 20.9 | 51.8 | 6.2 | 18.8 |

Volatile organic compounds were measured according to head space gas spectrometry/mass chromatography (GC-MS)
In this method a headspace sampler is interfaced with a gas chromatograph equipped with a mass selective detector.
The sample size is 0.1 grams of sample in a 22.5 ml headspace vial
Sampling conditioning temperature is 190° C. for 30 minutes
The detection limit for the components in the hot melt adhesives is 0.2 ppm
ND means not detectable.

TABLE 4

Inventive Samples

| Samples | Inventive 1 | Inventive 2 | Inventive 3 | Inventive 4 |
|---|---|---|---|---|
| Stripping | Yes | Yes | Yes | Yes |
| Pentaerythritol tetrakis(3-(3,5-di-tert-butyl-4-hydroxyphenyl)propionate | 0.90% | 0.62% | 0.62% | 0.62% |
| Tris(2,4-ditert-butylphenyl)phosphite | — | 0.30% | 0.30% | 0.30% |
| Bis(2,2,6,6,-tetramethyl-4-piperidyl)sebaceate | 0.10% | 0.08% | 0.08% | 0.08% |
|  | $C_9$-Partially hydrogenated | $C_9$-Partially hydrogenated | $C_9$-Partially hydrogenated | $C_9$-Fully hydrogenated |
| Methylene Chloride | ND | ND | ND | ND |
| Hexane | ND | ND | ND | ND |
| Chloroform | ND | ND | ND | ND |
| Cyclohexane | <0.2 | ND | ND | ND |
| Toluene | <0.2 | ND | ND | ND |
| Ethylcyclohexane | ND | ND | ND | ND |
| Ethylbenzene | <0.2 | ND | ND | ND |
| P-Xylene | ND | ND | ND | ND |
| O-Xylene | <0.2 | ND | ND | ND |
| M-Xylene | ND | ND | ND | ND |
| Styrene | 0.2 | ND | ND | ND |
| a-Methyl Styrene | 0.2 | ND | ND | ND |
| Vinyl Toluene | 0.2 | ND | ND | ND |
| Indene | 1.5 | ND | ND | ND |
| Tetrachloroethene | ND | ND | ND | ND |
| Trichloroethene | ND | ND | ND | ND |
| Total | 2.2 | ND | ND | ND |

Volatile organic compounds were measured according to head space gas spectrometry/mass chromatography (GC-MS)
In this method a headspace sampler is interfaced with a gas chromatograph equipped with a mass selective detector.
The sample size is 0.1 grams of sample in a 22.5 ml headspace vial
Sampling conditioning temperature is 190° C. for 30 minutes
The detection limit for the components in the hot melt adhesives is 0.2 ppm We can see in Table 4 that the levels of individual VOC of the inventive samples are much lower than that of comparative samples, especially for partially hydrogenated $C_9$ samples. The levels of these VOCs of trace chemicals in the inventive samples are also significantly lower than that of comparative samples.

Example 2—Hygiene Adhesives

Adhesive formulations were also prepared for hygiene applications as shown in Table 5. Resin samples were used from Example 1 as shown in Table 5 to prepare the adhesive formulations. These hot melt adhesives were prepared by mixing polymer, resin, antioxidant, and oil using a Z-blade mixer until a homogeneous mixture was obtained. The temperature during mixing was about 160° C.

TABLE 5

|  |  | Hygiene 1 (wt %) | Hygiene 2 (wt %) |
|---|---|---|---|
| Hydrocarbon resin | Partially Hydrogenated resin | 60 |  |
| Hydrocarbon resin | Partially Hydrogenated resin |  | 60 |
| Styrene-Butadiene-Styrene (SBS) Copolymer | Polimeri - Europrene® SolT6414 | 20 |  |
| Styrene-Isoprene-Styrene (SIS) Copolymer | Kraton® D1165 |  | 20 |
| Oil | Petro Canada - Puretol® 380D | 20 | 20 |
| Antioxidant | BASF - Irganox® 1010 | 0.2 | 0.2 |

Wt % is based on the weight of the adhesive composition.

Table 6 shows the volatile organic compound content of the comparative and inventive hygiene adhesives. The inventive hygiene adhesive samples had VOC levels of 0.9 ppm and non-detectable while the comparative hygiene adhesive samples had VOC levels of 64.8 ppm and 28.6 ppm.

TABLE 6

| Formulation | Hygiene 1 | Hygiene 2 | Hygiene 1 | Hygiene 2 |
|---|---|---|---|---|
| Resin Sample | Comparative 1 | Comparative 4 | Inventive 1 | Inventive 2 |
| Method of adhesive preparation | z-blade | z-blade | z-blade | z-blade |
| Methylene Chloride | <0.2 | ND | ND | ND |
| Hexane | <0.2 | ND | ND | ND |
| Chloroform | <0.2 | ND | ND | ND |
| Cyclohexane | 5.2 | 0.3 | ND | ND |
| Toluene | 8.5 | 26.4 | ND | 0.9 |
| Ethylcyclohexane | 2.6 | ND | ND | ND |
| Ethylbenzene | 1.9 | ND | ND | ND |
| P-Xylene | 0.8 | ND | ND | ND |
| O-Xylene | ND | ND | ND | ND |
| M-Xylene | ND | ND | ND | ND |
| Styrene | 7.1 | 0.2 | ND | ND |
| a-Methyl Styrene | 6.8 | 0.3 | ND | ND |
| Vinyl Toluene | 5.7 | 0.3 | ND | ND |
| Indene | 26.2 | 1.2 | ND | ND |
| Tetrachloroethene | ND | ND | ND | ND |
| Trichloroethene | ND | ND | ND | ND |
| Total | 64.8 | 28.6 | ND | 0.9 |

Example 3—Packaging Adhesives

Adhesive formulations were also prepared for packaging applications as shown in Table 7. Resin samples were used from Example 1 as shown in Table 8 to prepare the adhesive formulations. These hot melt adhesives were prepared by mixing polymer, resin, antioxidant, and oil on a hot plate until a homogeneous mixture was obtained. The temperature during mixing was about 160° C.

TABLE 7

Packaging Adhesive Formulation

| | | Packaging 1 (wt %) |
|---|---|---|
| Hydrocarbon resin | Partially Hydrogenated resin | 45 |
| EVA | Arkema - Evatane ® 28150 | 35 |
| Wax | Sasol - Sasol ® Wax H1 | 20 |
| Antioxidant | BASF - Irganox ® 1010 | 1 |

Wt % based on the adhesive composition

TABLE 8

Packaging Adhesive VOC Content

| Formulation | Packaging 1 | Packaging 1 |
|---|---|---|
| Resin Sample | Comparative 1 | Inventive 1 |
| Method of adhesive preparation | hot plate hand mixing | hot plate hand mixing |
| Samples | Comparative 1 | Developmental 1 |
| Methylene Chloride | ND | ND |
| Hexane | ND | ND |
| Chloroform | ND | ND |
| Cyclohexane | 0.2 | ND |
| Toluene | 0.5 | ND |
| Ethylcyclohexane | <0.2 | ND |
| Ethylbenzene | 0.4 | ND |
| P-Xylene | 0.2 | ND |
| O-Xylene | <0.2 | ND |
| M-Xylene | ND | ND |
| Styrene | 1.8 | <0.2 |
| a-Methyl Styrene | 0.5 | <0.2 |
| Vinyl Toluene | 1.4 | <0.2 |
| Indene | 7.7 | 0.7 |
| Tetrachloroethene | ND | ND |
| Trichloroethene | ND | ND |
| Total | 12.6 | 0.7 |

The data show that the inventive packaging adhesive had a VOC content of 0.7 ppm while the comparative sample had a VOC content of 12.6 ppm.

Example 4—Automotive Adhesives

Adhesive formulations were also prepared for automotive applications as shown in Table 9. Resin samples were used from Example 1 as shown in Table 10 to prepare the adhesive formulations. These hot melt adhesives were prepared by mixing polymer, resin, antioxidant, and oil on a hot plate or with a Z-Blade mixer until a homogeneous mixture was obtained. The temperature during mixing was about 160° C.

TABLE 9

Automotive Adhesives

| | | Automotive 1 (wt %) | Automotive 2 (wt %) |
|---|---|---|---|
| Hydrocarbon resin | Partially Hydrogenated resin | 60 | |
| Hydrocarbon resin | Partially Hydrogenated resin | | 53.5 |
| SBS | Polimeri - Europrene ® SolT6414 | 20 | |
| SBS | TSRC - Vector ® 4186 | | 36 |
| Amorphous Polyolefin (APO) | Eastman - Aerafin ® 180 | | |
| Oil | Petro Canada - Puretol ® 380D | 20 | 10 |
| Antioxidant | BASF - Irganox ® 1010 | 0.2 | |
| Antioxidant | BASF - Irganox ® B225 | | 0.5 |

Wt % is based on the adhesive composition.

TABLE 10

Automotive Adhesives VOC Content

| Formulation | Auto-motive - 1 | Auto-motive 2 | Auto-motive 1 | Auto-motive 2 |
|---|---|---|---|---|
| Resin Sample | Comparative 1 | Comparative 4 | Inventive 1 | Inventive 2 |
| Method of adhesive preparation | hot plate hand mixing | z-blade | hot plate hand mixing | z-blade |
| Methylene Chloride | <0.2 | ND | ND | ND |
| Hexane | <0.2 | ND | ND | ND |
| Chloroform | <0.2 | ND | ND | ND |
| Cyclohexane | 5.2 | 5.2 | ND | <0.2 |
| Toluene | 8.5 | 1.0 | ND | <0.2 |
| Ethylcyclohexane | 2.6 | 1.2 | ND | ND |
| Ethylbenzene | 1.9 | 0.3 | ND | ND |
| P-Xylene | 0.8 | 0.4 | ND | <0.2 |
| O-Xylene | ND | 1.3 | ND | ND |
| M-Xylene | ND | ND | ND | ND |
| Styrene | 7.1 | 1.5 | ND | ND |
| a-Methyl Styrene | 6.8 | 1.9 | ND | <0.2 |
| Vinyl Toluene | 5.7 | 0.8 | ND | ND |
| Indene | 26.2 | 6.8 | ND | <0.2 |
| Tetrachloroethene | ND | ND | ND | ND |
| Trichloroethene | ND | ND | ND | ND |
| Total | 64.8 | 20.4 | ND | <0.2 |

The data show that the inventive packaging adhesives had VOC contents of <0.2 ppm and not detectable while the comparative sample had VOC contents of 64.8 and 20.4 ppm.

That which is claimed:

1. A hygiene hot melt adhesive composition, comprising:
   at least at least one base polymer,
   about 20 to about 80 parts by weight of at least one tackifier composition, which comprises at least one thermoplastic hydrocarbon resin and an antioxidant composition,
   about 10 to about 40 parts by weight of at least one styrene block copolymer (SBC),
   0 to about 40 parts by weight of at least one plasticizing oil,
   optionally at least one wax,
   optionally at least one filler, and
   0 to about 1 part by weight of at least one additional antioxidant;
   wherein a portion of the volatile organic compounds in the thermoplastic hydrocarbon resin has been removed;

wherein the antioxidant composition comprises at least one primary antioxidant, at least one secondary antioxidant, and at least one hindered amine light stabilizer (HALS);

wherein the levels of individual volatile organic compounds in the at least one tackifier composition are less than about 0.5 ppm as measured by GC/MS headspace analysis;

wherein the at least one tackifier composition comprises at least one fully hydrogenated or partially hydrogenated C9 resin; and wherein a portion of the volatile organic compounds in the C9 resin has been removed.

2. The hygiene hot melt adhesive composition, of claim 1, wherein:

the at least one SBC is present in an amount of about 10 to about 30 parts by weight, and wherein the at least one tackifier is present in an amount of about 50 to about 70 parts by weight wherein the at least one plasticizer oil is present in an amount of about 10 to about 30 parts by weight.

3. The hygiene hot melt adhesive composition of claim 1, wherein the composition comprises:

(a) about 15 to about 25 parts by weight of the at least one SBC;

(b) about 55 to about 65 parts by weight of the at least one tackifier composition; and (c) about 15 to about 25 parts by weight of the at least one plasticizer oil.

4. The hygiene hot melt adhesive composition of claim 1, wherein the composition comprises about 20 to about 40 parts by weight of at the least one SBC.

5. The hygiene hot melt adhesive composition of claim 1, where the composition comprises:

(a) about 30 to about 40 parts by weight of the at least one SBC;

(b) about 30 to about 50 parts by weight of the at least one tackifier composition; and (c) about 10 to about 30 parts by weight of the at least one plasticizer oil.

6. A hygiene hot melt adhesive composition, comprising:

(a) about 20 to about 90 parts by weight of at least one metallocene polymer;

(b) about 10 to about 50 parts by weight of at least one tackifier composition;

wherein:

the tackifier composition comprises at least thermoplastic hydrocarbon resin;

a portion of the volatile organic compounds in the thermoplastic hydrocarbon resin has been removed;

the antioxidant composition comprises at least one primary antioxidant, and at least one hindered amine light stabilizer (HALS); and the levels of individual volatile organic compounds in the tackifier composition are less than about 0.5 ppm as measured by GC/MS headspace analysis;

(c) 0 to about 40 parts by weight of at least one oil;

(d) 0 about 40 parts by weight of at least one wax; and (e) 0 to 1 part by weight of at least one additional antioxidant, wherein the at least one tackifier composition comprises at least one fully hydrogenated or partially hydrogenated C9 resin; and wherein a portion of the volatile organic compounds in the C9 resin has been removed.

7. A hygiene hot melt adhesive composition, comprising:

(a) about 10 to about 50 parts by weight of an OBC polymer;

(b) about 30 to about 80 parts by weight of at least one tackifier composition;

wherein:

the tackifier composition comprises at least thermoplastic hydrocarbon resin;

a portion of the volatile organic compounds in the thermoplastic hydrocarbon resin has been removed;

the antioxidant composition comprises at least one primary antioxidant, and at least one hindered amine light stabilizer (HALS); and the levels of individual volatile organic compounds in the tackifier composition are less than about 0.5 ppm as measured by GC/MS headspace analysis;

(c) 0 to about 40 parts by weight of at least one oil;

(d) 0 to about 20 parts by weight of at least one wax; and (e) 0 to about 1 part by weight of at least one additional antioxidant, wherein the at least one tackifier composition comprises at least one fully hydrogenated or partially hydrogenated C9 resin; and wherein a portion of the volatile organic compounds in the C9 resin has been removed.

8. A hygiene hot melt adhesive composition, comprising:

(a) about 40 to about 90 parts by weight of at least one APAO polymer;

(b) about 10 to about 50 parts by weight of at least one tackifier composition, wherein:

the tackifier composition comprises at least thermoplastic hydrocarbon resin;

a portion of the volatile organic compounds in the thermoplastic hydrocarbon resin has been removed;

the antioxidant composition comprises at least one primary antioxidant, optionally at least one secondary antioxidant, and at least one hindered amine light stabilizer (HALS); and the levels of individual volatile organic compounds of interest in the tackifier composition are less than about 0.5 ppm as measured by GC/MS headspace analysis as described in this disclosure;

(c) 0 to about 20 parts by weight of at least one oil;

(d) 0 to about 20 parts by weight of at least one wax; and (e) 0 to about 1 part by weight of at least one additional antioxidant, wherein the at least one tackifier composition comprises at least one fully hydrogenated or partially hydrogenated C9 resin; and wherein a portion of the volatile organic compounds in the C9 resin has been removed.

9. The hygiene hot melt adhesive composition according to claim 1, wherein said primary antioxidant is at least one sterically hindered phenol selected from the group consisting of: (CI)-(CXIX):

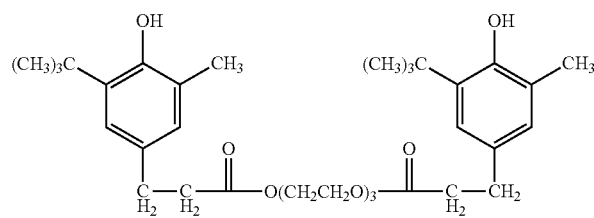
(CI)
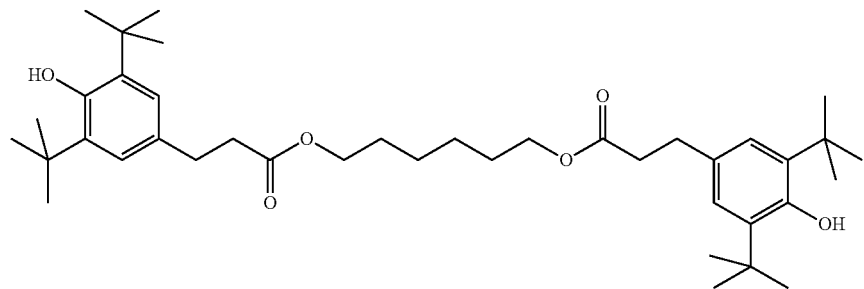
(CII)
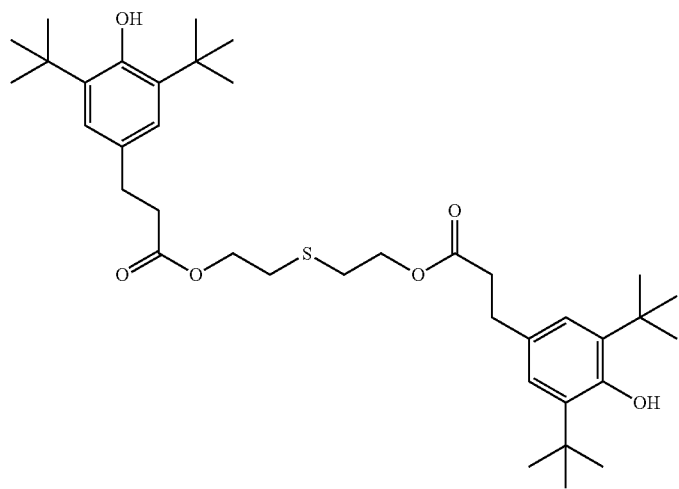
(CIII)
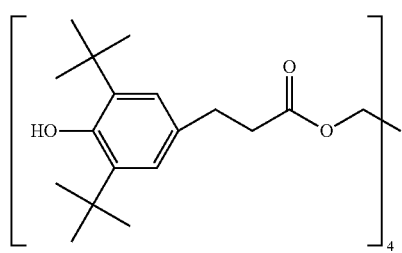
(CIV)
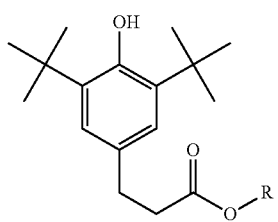
(CV)

wherein R=C₈H₁₇ or C₁₈H₃₇
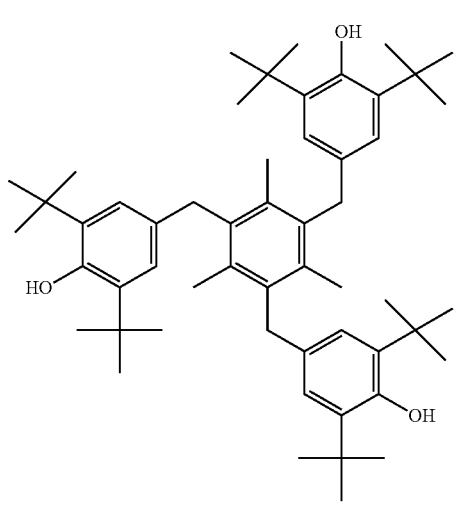
(CVI)
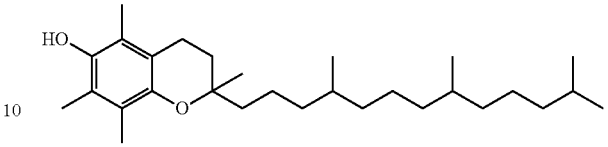
(CXI)
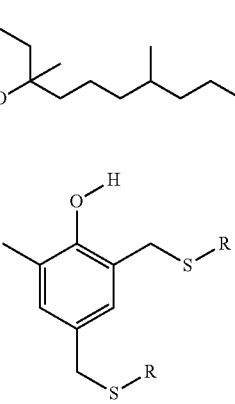
(CXII)
wherein R=C₈H₁₇ or C₁₂H₂₅;
(CVII)
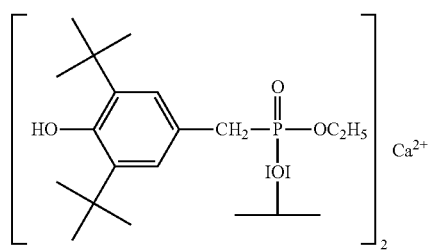
(CXIII)
(CVIII)
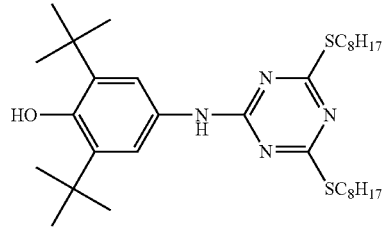
(CXIV)
(CIX)
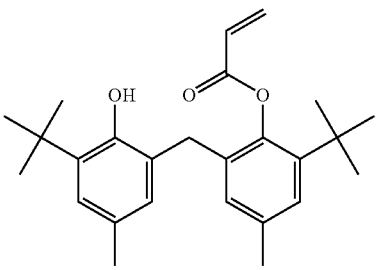
(CXV)
(CX)
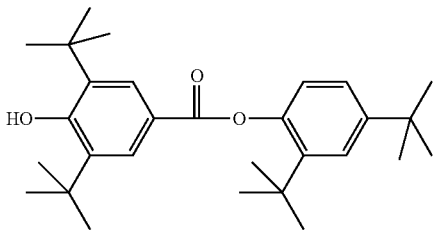
(CXVI)

-continued

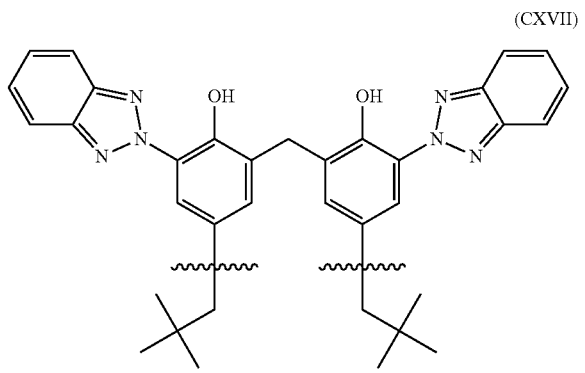
(CXVII)

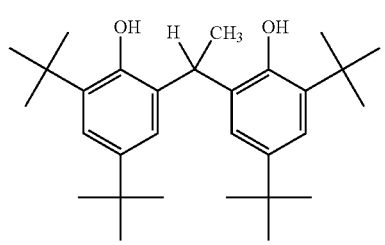
(CXVIII)

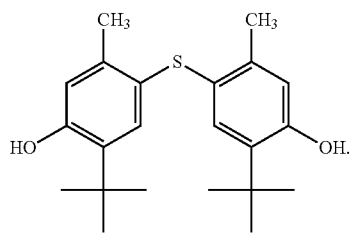
(CXIX)

10. The hygiene hot melt adhesive composition according to claim 1, wherein said secondary antioxidant is at least one selected from the group consisting of: organo-phosphites, thioethers, and hydroxyl-amines.

11. The hygiene hot melt adhesive composition according to claim 10, wherein said secondary antioxidant is selected from the group consisting of: 2,2',T-Nitrilo[triethyl-[3,3,5,5-tetra-tert.-butyl-1,1-biphenyl-2,2-diyl] phosphite (CAS 80410-33-9); Bis(2,4-di-tert.-butyl-6-methylphenyl)-ethyl-phosphite (CAS 145650-60-8); Bis-(2,4-ditert.-butylphenol) pentaerythritol diphosphate (CAS 26741-53-7); Tris(2,4-di-tert.butyl phenyl) phosphite (CAS 31570-04-4); Tetrakis(2,4-di-tert-butylphenyl)[1,1-biphenyl]-4,4'-diylbisphosphonite (CAS 119345-01-6); and Tri-(nonylphenyl)-phosphite.

12. The hygiene hot melt adhesive composition according to claim 10, wherein said thioethers are selected from the group consisting of: didodecyl-3,3'-thiodipropionate (CAS 123-28-4) and 3,3'-Thiodipropionic acid dioctadecylester (CAS 693-36-7).

13. The hygiene hot melt adhesive composition according to claim 10, wherein said hydroxyl-amines are oxidized bis(hydrogenated tallow alkyl) amines (CAS: 143925-92-2).

14. The hygiene hot melt adhesive composition according to claim 1, wherein said HALS is at least one selected from the group consisting of: (A1)-(AX):

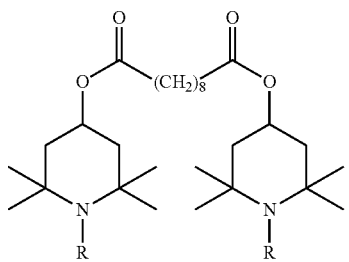
A-(I)

wherein R=H, $CH_3$ or $OC_8H_{17}$

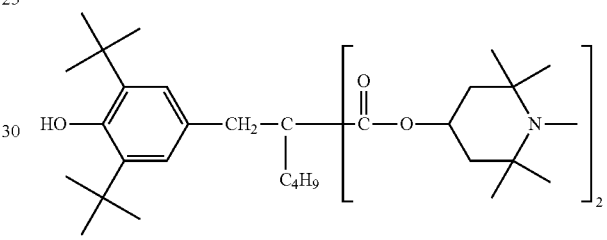
(AII)

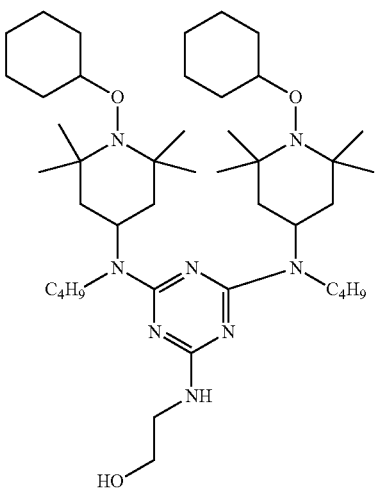
(AIII)

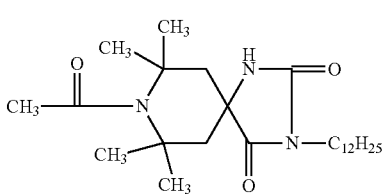
(AIV)

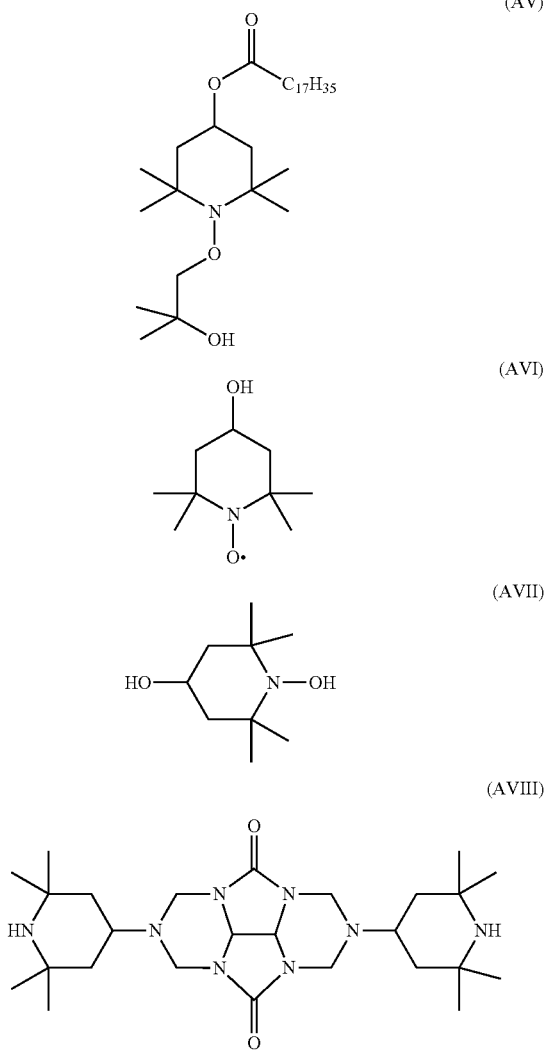

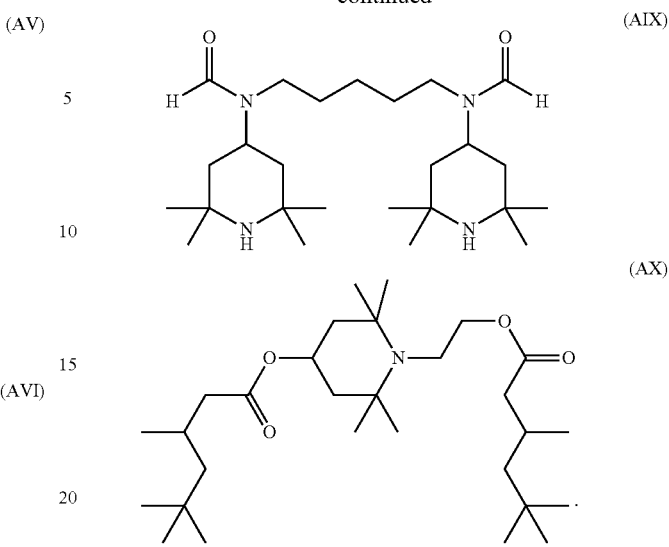

15. The hygiene hot melt adhesive composition according to claim 1, wherein said primary antioxidant is present in an amount of about 0.3% to about 1% based on the weight of the thermoplastic hydrocarbon resin.

16. The hygiene hot melt adhesive composition according to claim 1, wherein said secondary antioxidant is present in an amount of about 0.3% to about 1% based on the weight of said thermoplastic hydrocarbon resin.

17. The hygiene hot melt adhesive composition according to claim 1, wherein said HALS is present in an amount of about 0.05% to about 0.5% by weight based on the weight of said thermoplastic hydrocarbon resin.

18. The hygiene hot melt adhesive composition according to claim 1, wherein said primary antioxidant is pentaerythritol tetrakis(3-(3,5-di-tert-butyl-4-hydroxyphenyl)propionate), and wherein said secondary antioxidant is bis(2,2,6,6,-tetramethyl-4-piperidyl) sebacate.

19. An article comprising the hygiene hot melt adhesive composition of claim 1.

* * * * *